(12) United States Patent
Davis et al.

(10) Patent No.: US 9,205,143 B2
(45) Date of Patent: Dec. 8, 2015

(54) PNEUMOCOCCAL VACCINE AND USES THEREOF

(71) Applicant: COLEY PHARMACEUTICAL GROUP INC., New York, NY (US)

(72) Inventors: Heather Lynn Davis, Ottawa (CA); Arthur Mertz Krieg, Cambridge, MA (US); Nicolai Lohse, Hvidovre (DK); Lars Ostergaard, Aarhus N (DK); Henrik Carl Schonheyder, Aalborg (DK); Ole Schmeltz Sogaard, Aarhus N (DK)

(73) Assignee: Coley Pharmaceutical Group Inc., New York, NY (US)

( * ) Notice: Subject to any disclaimer, the term of this patent is extended or adjusted under 35 U.S.C. 154(b) by 0 days.

(21) Appl. No.: 14/049,842

(22) Filed: Oct. 9, 2013

(65) Prior Publication Data

US 2014/0099337 A1 Apr. 10, 2014

Related U.S. Application Data

(62) Division of application No. 13/266,846, filed as application No. PCT/IB2010/051150 on Mar. 17, 2010, now abandoned.

(60) Provisional application No. 61/238,313, filed on Aug. 31, 2009, provisional application No. 61/174,068, filed on Apr. 30, 2009.

(51) Int. Cl.
*A61K 39/385* (2006.01)
*A61K 39/02* (2006.01)
*A61K 39/09* (2006.01)
*A61K 39/00* (2006.01)

(52) U.S. Cl.
CPC ............. *A61K 39/092* (2013.01); *A61K 39/385* (2013.01); *A61K 2039/55561* (2013.01); *A61K 2039/6037* (2013.01)

(58) Field of Classification Search
CPC .... A61K 39/02; A61K 39/092; A61K 39/385
USPC ............................... 424/184.1, 193.1, 197.11
See application file for complete search history.

(56) References Cited

U.S. PATENT DOCUMENTS

| | | | |
|---|---|---|---|
| 4,469,863 A | 9/1984 | Ts'o et al. | |
| 4,709,017 A | 11/1987 | Collier et al. | |
| 4,950,740 A | 8/1990 | Greenfield et al. | |
| 5,023,243 A | 6/1991 | Tullis | |
| 5,843,711 A | 12/1998 | Collier et al. | |
| 5,917,017 A | 6/1999 | Collier et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,455,673 B1 | 9/2002 | Collier | |
| 7,074,415 B2 | 7/2006 | Hamel et al. | |
| 7,128,918 B1 | 10/2006 | Hamel et al. | |
| 7,709,001 B2 | 5/2010 | Hausdorff et al. | |
| 7,955,605 B2 | 6/2011 | Prasad | |
| 8,808,707 B1 * | 8/2014 | Siber et al. ............... | 424/197.11 |
| 2003/0148976 A1 | 8/2003 | Krieg et al. | |
| 2007/0184072 A1 | 8/2007 | Hausdorff et al. | |

FOREIGN PATENT DOCUMENTS

| | | |
|---|---|---|
| EP | 0378881 | 7/1990 |
| EP | 0471177 | 2/1992 |
| GB | WO2007/000342 | * 1/2007 |
| GB | WO2007/071707 | * 6/2007 |
| WO | WO8301451 | 4/1983 |
| WO | WO8706838 | 11/1987 |
| WO | WO9101146 | 2/1991 |
| WO | WO9602555 | 2/1996 |
| WO | WO9818810 | 5/1998 |
| WO | WO9933488 | 7/1999 |
| WO | WO9952549 | 10/1999 |
| WO | WO0037105 | 6/2000 |
| WO | WO0121207 | 3/2001 |
| WO | WO0122990 | 4/2001 |
| WO | WO03024480 | 3/2003 |
| WO | WO03054007 | 7/2003 |
| WO | WO2004081515 | 9/2004 |
| WO | WO2006110352 | 10/2006 |
| WO | WO2006110381 | 10/2006 |
| WO | WO2006134423 | 12/2006 |
| WO | WO2007026190 | 3/2007 |
| WO | WO2007095316 | 8/2007 |
| WO | WO2007127665 | 11/2007 |
| WO | WO2008045852 | 4/2008 |
| WO | WO2008079653 | 7/2008 |
| WO | WO2008079732 | 7/2008 |
| WO | WO2008112868 | 9/2008 |
| WO | WO2008118752 | 10/2008 |
| WO | WO2008143709 | 11/2008 |
| WO | WO2009000826 | 12/2008 |
| WO | WO2010080484 | 7/2010 |
| WO | WO2010080486 | 7/2010 |

OTHER PUBLICATIONS

K. Klugman, et al, N. Engl J Med. 349:1341-8, 2003.*
Sen et al, Infect Immun. Apr. 2006;74(4):2177-86.*

(Continued)

*Primary Examiner* — Padma V Baskar
(74) *Attorney, Agent, or Firm* — Matthew J. Pugmire

(57) ABSTRACT

The present invention relates to new pneumococcal vaccines. The invention also relates to vaccination of subjects, in particular immunocompromised subjects, against pneumoccocal infections using said novel pneumococcal vaccines.

15 Claims, 9 Drawing Sheets

(56) References Cited

OTHER PUBLICATIONS

Baraldo, K., et al., "N19 Polyepitope as a Carrier for Enhanced Immunogenicity and Protective Efficacy of Meningococcal Conjugate Vaccines", Infection and Immunity, 2004, 4884-4887, vol. 72, No. 8.
Chu, R., et al., "CpG Oligodeoxynucleotides Act as Adjuvants for Pneumococcal Polysaccharide-Protein Conjugate Vaccines and Enhance Antipolysaccharide Immunoglobulin G2a (IgG2a) and IgG3 Antibodies", Infection and Immunity, 2000, 1450-1456, vol. 68, No. 3.
Falugi, F., et al., "Rationally designed strings of promiscuous CD4+ T cell epitopes provide help to Haemophilus influenzae type b oligosaccharide: a model for new conjugate vaccines", Eur. J. Immunol., 2001, 3816-3824, vol. 31.
Jones, C., "Vaccines based on the cell surface carbohydrates of pathogenic bacteria," Annals of the Brazilian Academy of Sciences, 2005, 293-324, vol. 77, No. 2.
Krieg, A., "Therapeutic potential of Toll-like receptor 9 activation," Nature Reviews, 2006, 471-484, vol. 5.
Kuo, J., "Characterization of a Recombinant Pneumolysin and Its Use as a Protein Carrier for Pneumococcal Type 18C Conjugate Vaccines", Infection and Immunity, 1995, 2706-2713, vol. 63, No. 7.
Sjolander, A., et al., "ISCOMs: an adjuvant with multiple functions," Journal of Leukocyte Biology, 1998, 713-723, vol. 64.
Uchida, T., et al., "Mutation in the Structural Gene for Diphtheria Toxin carried by Temperate Phage β," Nature New Biology, 1971, 8-11, vol. 233.
Uchida, T., et al., "Diphtheria Toxin and Related Proteins: I. Isolation and properties of mutant proteins serologically related to diphtheria toxin," Journal Biol. Chem., 1973, 3838-3844, vol. 248, No. 11.
Krieg, A.M., et al., "CpG Motifs in Bacterial DNA Trigger Direct B-Cell Activation", Nature, 374:546-549 (1995).
Ballas, Z.K., et al., "Induction of NK Activity in Murine and Human Cells by CpG Motifs in Oligodeoxynucleotides and Bacterial DNA", J. Immunol., 157:1840-1845 (1996).
Krieg, A.M., et al., "Sequence Motifs in Adenoviral DNA Block Immune Activation by Stimulatory CpG Motifs", Proc. Natl. Acad. Sci. USA, 95:12631-12636 (1998).
Goodchild, J., "Conjugates of Oligoncleotides and Modified Oligonucleotides: A Review of Their Synthesis and Properties", Bioconjuqate Chem., 1(3):165-187 (1990).
Crooke, ST., et al., "Progress in Antisense Oligonucleotide Therapeutics", Annu. Rev. Pharmacol. Toxicol., 36:107-129 (1996).
Hunziker, J., et al., "Nucleic Acid Analogues: Synthesis and Properties", Mod. Synth. Methods, 7:331-417(1995).
Cooper, C.L., et al., "CPG 7909 Adjuvant plus Hepatitis B Virus Vaccination in HIV-Infected Adults Achieves Long-Term Seroprotection for Up to 5 Years", Clinical Infectious Diseases, 46(8):1310-1314 (2008).
Kroon, F.P., et al., "Enhanced Antibody Response to Pneumococcal Polysaccharide Vaccine after Prior Immunization with Conjugate Pneumococcal Vaccine in HIV-Infected Adults", Vaccine, 19(7-8):886-894 (2000).
Feikin, DR., et al., "Specificity of the Antibody Response to the Pneumococcal Polysaccharide and Conjugate Vaccines in Human Immunodeficiency Virus-Infected Adults", Clinical and Diagnostic Laboratory Immunoloqy, 11 (1):137-141 (2004).
Cordonnier, C., et al., "Randomized Study of Early versus Late Immunization with Pneumococal Conjugate Vaccine after Allogeneic Stem Cell Transplantation", Clinical Infectious Diseases, 48(10):1392-1401 (2009).
Centers for Disease Control and Prevention (CDC), "Pneumococcal Vaccination for Cochlear Implant Candidates and Recipients: Updated Recommendations of the Advisory Committee on Immunization Practices", Morbility and Mortality Weekly Report, 52(31):739-740 (2003).
Angel, J.B., et al., "CpG Increases Vaccine Antigen-Specific Cell-Mediated Immunity when Administered with Hepatitis B Vaccine in HIV Infection", Journal of Immune Based Therapies and Vaccines, 6:4 (2008).
Sogaard, O.S., et al., "Improving the Ummunogenicity of Pneumococcal Conjugate Vaccine in HIV-Infected Adults with a Toll-Like Receptor 9 Agonist Adjuvant: A Randomized, Controlled Trial", Clinical Infectious Diseases, 51( 1):42-50 (2010).
"CpG 7909: PF 3512676, PF-3512676", Drugs in R&D, 7(5):312-316 (2006).
Gupta, K., et al., "A Review of the Role of CpG Oligodeoxynucleotides as Toll-Like Receptor 9 Agonists in Prophylactic and Therapeutic Vaccine Development in Infectious Diseases", Drugs in R&D, 9(3):137-145 (2008).
Uhlmann, E., et al., "Antisense Oligonucleotides: A New Therapeutic Principle", Chemical Reviews, 90(4):543-584 (1990).
Yamamoto, S., et al., "Unique Palindromic Sequences in Synthetic Oligonucleotides are Required to Induce INF and Augment INF-Mediated Natural Killer Activity", J. Immunol., 148(12):4072-4076 (1992).

\* cited by examiner

```
                              SEQUENCE LISTING

<160> NUMBER OF SEQ ID NOS: 40

<210> SEQ ID NO 1
<211> LENGTH: 20
<212> TYPE: DNA
<213> ORGANISM: Artificial
<220> FEATURE:
<223> OTHER INFORMATION: A class CpG oligonucleotide

<400> SEQUENCE: 1
ggggacgacg tcgtggggggg                                                     20

<210> SEQ ID NO 2
<211> LENGTH: 21
<212> TYPE: DNA
<213> ORGANISM: Artificial
<220> FEATURE:
<223> OTHER INFORMATION: A class CpG oligonucleotide
<220> FEATURE:
<221> NAME/KEY: Phosphorothioate bond
<222> LOCATION: (1)..(3)
<220> FEATURE:
<221> NAME/KEY: Phosphorothioate bond
<222> LOCATION: (16)..(21)

<400> SEQUENCE: 2
ggggacgacg tcgtggggggg g                                                   21

<210> SEQ ID NO 3
<211> LENGTH: 21
<212> TYPE: DNA
<213> ORGANISM: Artificial
<220> FEATURE:
<223> OTHER INFORMATION: B class CpG oligonucleotide

<400> SEQUENCE: 3
tcgtcgtttt tcggtgcttt t                                                    21

<210> SEQ ID NO 4
<211> LENGTH: 21
<212> TYPE: DNA
<213> ORGANISM: Artificial
<220> FEATURE:
<223> OTHER INFORMATION: B class CpG oligonucleotide

<400> SEQUENCE: 4
tcgtcgtttt tcggtcgttt t                                                    21

<210> SEQ ID NO 5
<211> LENGTH: 24
<212> TYPE: DNA
<213> ORGANISM: Artificial
<220> FEATURE:
```

<223> OTHER INFORMATION: B class CpG oligonucleotide

<400> SEQUENCE: 5
tcgtcgtttt gtcgttttgt cgtt                                          24

<210> SEQ ID NO 6
<211> LENGTH: 24
<212> TYPE: DNA
<213> ORGANISM: Artificial
<220> FEATURE:
<223> OTHER INFORMATION: B class CpG oligonucleotide

<400> SEQUENCE: 6
tcgtcgtttc gtcgttttgt cgtt                                          24

<210> SEQ ID NO 7
<211> LENGTH: 24
<212> TYPE: DNA
<213> ORGANISM: Artificial
<220> FEATURE:
<223> OTHER INFORMATION: B class CpG oligonucleotide

<400> SEQUENCE: 7
tcgtcgtttt gtcgtttttt tcga                                          24

<210> SEQ ID NO 8
<211> LENGTH: 21
<212> TYPE: DNA
<213> ORGANISM: Artificial
<220> FEATURE:
<223> OTHER INFORMATION: B class CpG oligonucleotide
<220> FEATURE:
<221> NAME/KEY: Phosphorothioate bond
<222> LOCATION: (1)..(21)

<400> SEQUENCE: 8
tcgtcgtttt tcggtgcttt t                                             21

<210> SEQ ID NO 9
<211> LENGTH: 21
<212> TYPE: DNA
<213> ORGANISM: Artificial
<220> FEATURE:
<223> OTHER INFORMATION: B class CpG oligonucleotide
<220> FEATURE:
<221> NAME/KEY: Phosphorothioate bond
<222> LOCATION: (1)..(21)

<400> SEQUENCE: 9
tcgtcgtttt tcggtcgttt t                                             21

<210> SEQ ID NO 10
<211> LENGTH: 24
<212> TYPE: DNA
<213> ORGANISM: Artificial
<220> FEATURE:
<223> OTHER INFORMATION: B class CpG oligonucleotide
<220> FEATURE:
<221> NAME/KEY: Phosphorothioate bond
<222> LOCATION: (1)..(24)

<400> SEQUENCE: 10
tcgtcgtttt gtcgttttgt cgtt                                          24

<210> SEQ ID NO 11
<211> LENGTH: 24
<212> TYPE: DNA

```
<213> ORGANISM: Artificial
<220> FEATURE:
<223> OTHER INFORMATION: B class CpG oligonucleotide
<220> FEATURE:
<221> NAME/KEY: Phosphorothioate bond
<222> LOCATION: (1)..(24)

<400> SEQUENCE: 11
tcgtcgtttc gtcgttttgt cgtt                                          24

<210> SEQ ID NO 12
<211> LENGTH: 24
<212> TYPE: DNA
<213> ORGANISM: Artificial
<220> FEATURE:
<223> OTHER INFORMATION: B class CpG oligonucleotide
<220> FEATURE:
<221> NAME/KEY: Phosphorothioate bond
<222> LOCATION: (1)..(24)

<400> SEQUENCE: 12
tcgtcgtttt gtcgtttttt tcga                                          24

<210> SEQ ID NO 13
<211> LENGTH: 22
<212> TYPE: DNA
<213> ORGANISM: Artificial
<220> FEATURE:
<223> OTHER INFORMATION: C class CpG oligonucleotide

<400> SEQUENCE: 13
tcgcgtcgtt cggcgcgcgc cg                                            22

<210> SEQ ID NO 14
<211> LENGTH: 23
<212> TYPE: DNA
<213> ORGANISM: Artificial
<220> FEATURE:
<223> OTHER INFORMATION: C class CpG oligonucleotide

<400> SEQUENCE: 14
tcgtcgacgt tcggcgcgcg ccg                                           23

<210> SEQ ID NO 15
<211> LENGTH: 21
<212> TYPE: DNA
<213> ORGANISM: Artificial
<220> FEATURE:
<223> OTHER INFORMATION: C class CpG oligonucleotide

<400> SEQUENCE: 15
tcggacgttc ggcgcgcgcc g                                             21

<210> SEQ ID NO 16
<211> LENGTH: 19
<212> TYPE: DNA
<213> ORGANISM: Artificial
<220> FEATURE:
<223> OTHER INFORMATION: C class CpG oligonucleotide

<400> SEQUENCE: 16
tcggacgttc ggcgcgccg                                                19

<210> SEQ ID NO 17
<211> LENGTH: 20
<212> TYPE: DNA
<213> ORGANISM: Artificial
```

```
<220> FEATURE:
<223> OTHER INFORMATION: C class CpG oligonucleotide

<400> SEQUENCE: 17
tcgcgtcgtt cggcgcgccg                                             20

<210> SEQ ID NO 18
<211> LENGTH: 20
<212> TYPE: DNA
<213> ORGANISM: Artificial
<220> FEATURE:
<223> OTHER INFORMATION: C class CpG oligonucleotide

<400> SEQUENCE: 18
tcgacgttcg gcgcgcgccg                                             20

<210> SEQ ID NO 19
<211> LENGTH: 18
<212> TYPE: DNA
<213> ORGANISM: Artificial
<220> FEATURE:
<223> OTHER INFORMATION: C class CpG oligonucleotide

<400> SEQUENCE: 19
tcgacgttcg gcgcgccg                                               18

<210> SEQ ID NO 20
<211> LENGTH: 18
<212> TYPE: DNA
<213> ORGANISM: Artificial
<220> FEATURE:
<223> OTHER INFORMATION: C class CpG oligonucleotide

<400> SEQUENCE: 20
tcgcgtcgtt cggcgccg                                               18

<210> SEQ ID NO 21
<211> LENGTH: 22
<212> TYPE: DNA
<213> ORGANISM: Artificial
<220> FEATURE:
<223> OTHER INFORMATION: C class CpG oligonucleotide

<400> SEQUENCE: 21
tcgcgacgtt cggcgcgcgc cg                                          22

<210> SEQ ID NO 22
<211> LENGTH: 22
<212> TYPE: DNA
<213> ORGANISM: Artificial
<220> FEATURE:
<223> OTHER INFORMATION: C class CpG oligonucleotide

<400> SEQUENCE: 22
tcgtcgtttt cggcgcgcgc cg                                          22

<210> SEQ ID NO 23
<211> LENGTH: 22
<212> TYPE: DNA
<213> ORGANISM: Artificial
<220> FEATURE:
<223> OTHER INFORMATION: C class CpG oligonucleotide

<400> SEQUENCE: 23
tcgtcgtttt cggcggccgc cg                                          22
```

```
<210> SEQ ID NO 24
<211> LENGTH: 24
<212> TYPE: DNA
<213> ORGANISM: Artificial
<220> FEATURE:
<223> OTHER INFORMATION: C class CpG oligonucleotide

<400> SEQUENCE: 24
tcgtcgtttt acggcgccgt gccg                                          24

<210> SEQ ID NO 25
<211> LENGTH: 23
<212> TYPE: DNA
<213> ORGANISM: Artificial
<220> FEATURE:
<223> OTHER INFORMATION: C class CpG oligonucleotide

<400> SEQUENCE: 25
tcgtcgtttt cggcgcgcgc cgt                                           23

<210> SEQ ID NO 26
<211> LENGTH: 22
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(4)
<220> FEATURE:
<221> NAME/KEY: Phosphorothioate bond
<222> LOCATION: (8)..(11)
<220> FEATURE:
<221> NAME/KEY: Phosphorothioate bond
<222> LOCATION: (12)..(16)
<220> FEATURE:
<221> NAME/KEY: Phosphorothioate bond
<222> LOCATION: (17)..(22)

<400> SEQUENCE: 26
tcgcgtcgtt cggcgcgcgc cg                                            22

<210> SEQ ID NO 27
<211> LENGTH: 23
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(5)
<220> FEATURE:
<221> NAME/KEY: Phosphorothioate bond
<222> LOCATION: (6)..(8)
<220> FEATURE:
<221> NAME/KEY: Phosphorothioate bond
<222> LOCATION: (9)..(12)
<220> FEATURE:
<221> NAME/KEY: Phosphorothioate bond
<222> LOCATION: (13)..(17)
<220> FEATURE:
<221> NAME/KEY: Phosphorothioate bond
<222> LOCATION: (18)..(23)

<400> SEQUENCE: 27
```
tcgtcgacgt tcggcgcgcg ccg                                                23

<210> SEQ ID NO 28
<211> LENGTH: 21
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(6)
<220> FEATURE:
<221> NAME/KEY: Phosphorothioate bond
<222> LOCATION: (7)..(10)
<220> FEATURE:
<221> NAME/KEY: Phosphorothioate bond
<222> LOCATION: (11)..(15)
<220> FEATURE:
<221> NAME/KEY: Phosphorothioate bond
<222> LOCATION: (16)..(21)

<400> SEQUENCE: 28
tcggacgttc ggcgcgcgcc g                                                  21

<210> SEQ ID NO 29
<211> LENGTH: 19
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(6)
<220> FEATURE:
<221> NAME/KEY: Phosphorothioate bond
<222> LOCATION: (7)..(10)
<220> FEATURE:
<221> NAME/KEY: Phosphorothioate bond
<222> LOCATION: (11)..(19)

<400> SEQUENCE: 29
tcggacgttc ggcgcgccg                                                     19

<210> SEQ ID NO 30
<211> LENGTH: 20
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(4)
<220> FEATURE:
<221> NAME/KEY: Phosphorothioate bond
<222> LOCATION: (5)..(7)
<220> FEATURE:
<221> NAME/KEY: Phosphorothioate bond
<222> LOCATION: (8)..(11)
<220> FEATURE:
<221> NAME/KEY: Phosphorothioate bond
<222> LOCATION: (12)..(20)

<400> SEQUENCE: 30
tcgcgtcgtt cggcgcgccg                                                    20

```
<210> SEQ ID NO 31
<211> LENGTH: 20
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(5)
<220> FEATURE:
<221> NAME/KEY: Phosphorothioate bond
<222> LOCATION: (6)..(9)
<220> FEATURE:
<221> NAME/KEY: Phosphorothioate bond
<222> LOCATION: (10)..(14)
<220> FEATURE:
<221> NAME/KEY: Phosphorothioate bond
<222> LOCATION: (15)..(20)

<400> SEQUENCE: 31
tcgacgttcg gcgcgcgccg                                                    20

<210> SEQ ID NO 32
<211> LENGTH: 18
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(5)
<220> FEATURE:
<221> NAME/KEY: Phosphorothioate bond
<222> LOCATION: (6)..(9)
<220> FEATURE:
<221> NAME/KEY: Phosphorothioate bond
<222> LOCATION: (10)..(18)

<400> SEQUENCE: 32
tcgacgttcg gcgcgccg                                                      18

<210> SEQ ID NO 33
<211> LENGTH: 18
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(4)
<220> FEATURE:
<221> NAME/KEY: Phosphorothioate bond
<222> LOCATION: (5)..(7)
<220> FEATURE:
<221> NAME/KEY: Phosphorothioate bond
<222> LOCATION: (8)..(11)
<220> FEATURE:
<221> NAME/KEY: Phosphorothioate bond
<222> LOCATION: (12)..(18)

<400> SEQUENCE: 33
tcgcgtcgtt cggcgccg                                                      18
```

```
<210> SEQ ID NO 34
<211> LENGTH: 22
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(4)
<220> FEATURE:
<221> NAME/KEY: Phosphorothioate bond
<222> LOCATION: (5)..(7)
<220> FEATURE:
<221> NAME/KEY: Phosphorothioate bond
<222> LOCATION: (8)..(11)
<220> FEATURE:
<221> NAME/KEY: Phosphorothioate bond
<222> LOCATION: (12)..(16)
<220> FEATURE:
<221> NAME/KEY: Phosphorothioate bond
<222> LOCATION: (17)..(22)

<400> SEQUENCE: 34
tcgcgacgtt cggcgcgcgc cg                                              22

<210> SEQ ID NO 35
<211> LENGTH: 22
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(22)

<400> SEQUENCE: 35
tcgtcgtttt cggcgcgcgc cg                                              22

<210> SEQ ID NO 36
<211> LENGTH: 22
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(22)

<400> SEQUENCE: 36
tcgtcgtttt cggcggccgc cg                                              22

<210> SEQ ID NO 37
<211> LENGTH: 24
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(5)
<220> FEATURE:
<221> NAME/KEY: Phosphorothioate bond
<222> LOCATION: (6)..(12)
<220> FEATURE:
<221> NAME/KEY: Phosphorothioate bond
<222> LOCATION: (13)..(18)
<220> FEATURE:
<221> NAME/KEY: Phosphorothioate bond
<222> LOCATION: (19)..(24)
```

<400> SEQUENCE: 37
tcgtcgtttt acggcgccgt gccg        24

<210> SEQ ID NO 38
<211> LENGTH: 23
<212> TYPE: DNA
<213> ORGANISM: Artificial
<220> FEATURE:
<223> OTHER INFORMATION: C class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(23)

<400> SEQUENCE: 38
tcgtcgtttt cggcgcgcgc cgt        23

<210> SEQ ID NO 39
<211> LENGTH: 23
<212> TYPE: DNA
<213> ORGANISM: Artificial
<220> FEATURE:
<223> OTHER INFORMATION: P class CpG oligonucleotide

<400> SEQUENCE: 39
tcgtcgacga tcggcgcgcg ccg        23

<210> SEQ ID NO 40
<211> LENGTH: 23
<212> TYPE: DNA
<213> ORGANISM: Artificial
<220> FEATURE:
<223> OTHER INFORMATION: P class CpG oligonucleotide
<220> FEATURE:
<221> NAME/KEY: Phosphorothioate bond
<222> LOCATION: (1)..(2)
<220> FEATURE:
<221> NAME/KEY: Phosphorothioate bond
<222> LOCATION: (3)..(5)
<220> FEATURE:
<221> NAME/KEY: Phosphorothioate bond
<222> LOCATION: (6)..(8)
<220> FEATURE:
<221> NAME/KEY: Phosphorothioate bond
<222> LOCATION: (9)..(12)
<220> FEATURE:
<221> NAME/KEY: Phosphorothioate bond
<222> LOCATION: (13)..(17)
<220> FEATURE:
<221> NAME/KEY: Phosphorothioate bond
<222> LOCATION: (18)..(23)

<400> SEQUENCE: 40
tcgtcgacga tcggcgcgcg ccg        23

PNEUMOCOCCAL VACCINE AND USES THEREOF

CROSS REFERENCE TO RELATED APPLICATIONS

This application is a divisional application of U.S. application Ser. No. 13/266,846, filed Oct. 28, 2011(now abandoned), which is the National Stage of International Application No. PCT/IB2010/051150, filed Mar. 17, 2010, which claims the benefit of U.S. Provisional Application No. 61/174,068, filed Apr. 30, 2009, and U.S. Provisional Application No. 61/238,313, filed Aug. 31, 2009, all of which are incorporated herein by reference.

REFERENCE TO SEQUENCE LISTING

This application is being filed electronically via EFS-Web and includes an electronically submitted sequence listing in .txt format. The .txt file contains a sequence listing entitled "PC33894B_Sequence_Listing_ST25.txt" created on Oct. 8, 2013 and having a size of 11.5 KB. The sequence listing contained in this .txt file is part of the specification and is herein incorporated by reference in its entirety.

FIELD OF THE INVENTION

The present invention relates to new pneumococcal vaccines. The invention also relates to vaccination of subjects, in particular immunocompromised subjects, against pneumoccocal infections using said novel pneumococcal vaccines.

BACKGROUND OF THE INVENTION

Pneumococcal diseases are a major public health problem all over the world. Infections caused by pneumococci are a major cause of morbidity and mortality all over the world. Pneumonia, febrile bacteraemia and meningitis are the most common manifestations of invasive pneumococcal disease, whereas bacterial spread within the respiratory tract may result in middle-ear infection, sinusitis or recurrent bronchitis. Compared with invasive disease, the non-invasive manifestations are usually less severe, but considerably more common.

In spite of the importance of pneumococcal disease, there is a scarcity of information on disease burden, particularly from developing countries. This is partly due to the inherent problem of obtaining an etiological diagnosis in cases of pneumonia. However, based on available data, acute respiratory infections kill an estimated 2.6 million children under five years of age annually. The pneumococcus causes over 1 million of these deaths, most of which occur in developing countries, where the pneumococcus is probably the most important pathogen of early infancy. In Europe and the United States, pneumococcal pneumonia is the most common community-acquired bacterial pneumonia, estimated to affect approximately 100 per 100 000 adults each year. The corresponding figures for febrile bacteraemia and meningitis are 15-19 per 100 000 and 1-2 per 100 000, respectively. The risk for one or more of these manifestations is much higher in infants and elderly people, as well as immune compromised persons of any age. Even in economically developed regions, invasive pneumococcal disease carries high mortality; for adults with pneumococcal pneumonia the mortality rate averages 10%-20%, whilst it may exceed 50% in the high-risk groups. Pneumonia is by far the most common cause of pneumococcal death worldwide.

The etiological agent of pneumococcal diseases, *Streptococcus pneumoniae* (the pneumococcus) a Gram-positive encapsulated coccus, surrounded by a polysaccharide capsule. Differences in the composition of this capsule permit serological differentiation between about 90 capsular types, some of which are frequently associated with pneumococcal disease, others rarely. Invasive pneumococcal infections include pneumonia, meningitis and febrile bacteremia; among the common non-invasive manifestations are otitis media, sinusitis and bronchitis.

Pneumococcal resistance to essential antimicrobials such as penicillins, cephalosporins and macrolides is a serious and rapidly increasing problem worldwide.

Conditions associated with increased risk of serious pneumococcal disease include age extremes (infants, elderly) and being immunocompromised for any reason, including but not limited to: HIV infection, other chronic viral infections, sickle-cell anaemia, diabetes, cancer and cancer therapy, smoking, chronic organ failures, organ transplant and immune suppressive therapy.

The recent development of widespread microbial resistance to essential antibiotics and the increasing number of immunocompromised persons underline the urgent need for more efficient pneumococcal vaccines.

Some of the shortcomings of current vaccination include: need for several boosts to achieve protection, delay in rise of protective antibodies, prevalence of vaccine non-responders (this is particularly a problem for immune-compromised individuals), cost of antigen and vaccine production which is a very significant limitation in the development of new conjugated pneumococcal vaccines, poorly protective antibodies with low affinity, falling antibody titres over time.

An object of the new pneumococcal vaccine of the invention is to overcome at least partially some of these shortcomings. In particular with a view to vaccinate immunocompromised subjects against pneumoccocal infections.

SUMMARY OF THE INVENTION

In a first aspect the present invention is directed towards new pneumococcal vaccines wherein said vaccine comprises one or more pneumoccal polysaccharide antigens conjugated to a carrier protein as antigen and an agonist for Toll-like receptor 9 (TLR9) as adjuvant.

In a further aspect, the present invention is directed towards the use of a pneumococcal vaccine comprising one or more pneumoccal polysaccharide antigens conjugated to a carrier protein as antigen and a TLR-9 agonist as adjuvant to vaccinate immunocompromised subjects.

In an aspect the invention is directed towards any of the pneumococcal vaccine disclosed herein for use in the vaccination of immunocompromised subjects, preferably any of the immunocompromised subjects disclosed herein.

In a further aspect, the present invention is directed towards the use of any of the pneumococcal vaccines disclosed herein to vaccinate immunocompromised subjects, preferably any of the immunocompromised subjects disclosed herein.

In a further aspect, the present invention is directed towards any of the vaccines disclosed herein for the prevention or treatment of diseases caused by *S. pneumoniae* infection, preferably in an immunocompromised subject.

In a further aspect, the present invention is directed towards a method of immunizing a subject, preferably any of the immunocompromised subjects disclosed herein, against diseases caused by *S. pneumoniae* infection comprising administering to said subject an immunoprotective dose of any of the vaccines disclosed herein.

In a further aspect, the present invention is directed towards the use of any of the vaccines disclosed herein, for the manufacture of a medicament for the prevention or treatment of diseases caused by S. pneumoniae infection, preferably in an immunocompromised subject.

In a further aspect, the present invention is directed towards any of the pneumococcal vaccines disclosed herein and at least one TLR-9 agonist disclosed herein.

In a further aspect, the present invention is directed towards any of the pneumococcal vaccines disclosed herein and at least one TLR-9 agonist disclosed herein for use in the vaccination of any of the immunocompromised subjects disclosed herein.

TOLL-LIKE RECEPTOR 9 AGONIST (TLR-9 AGONIST) OF THE INVENTION

Figure 1:
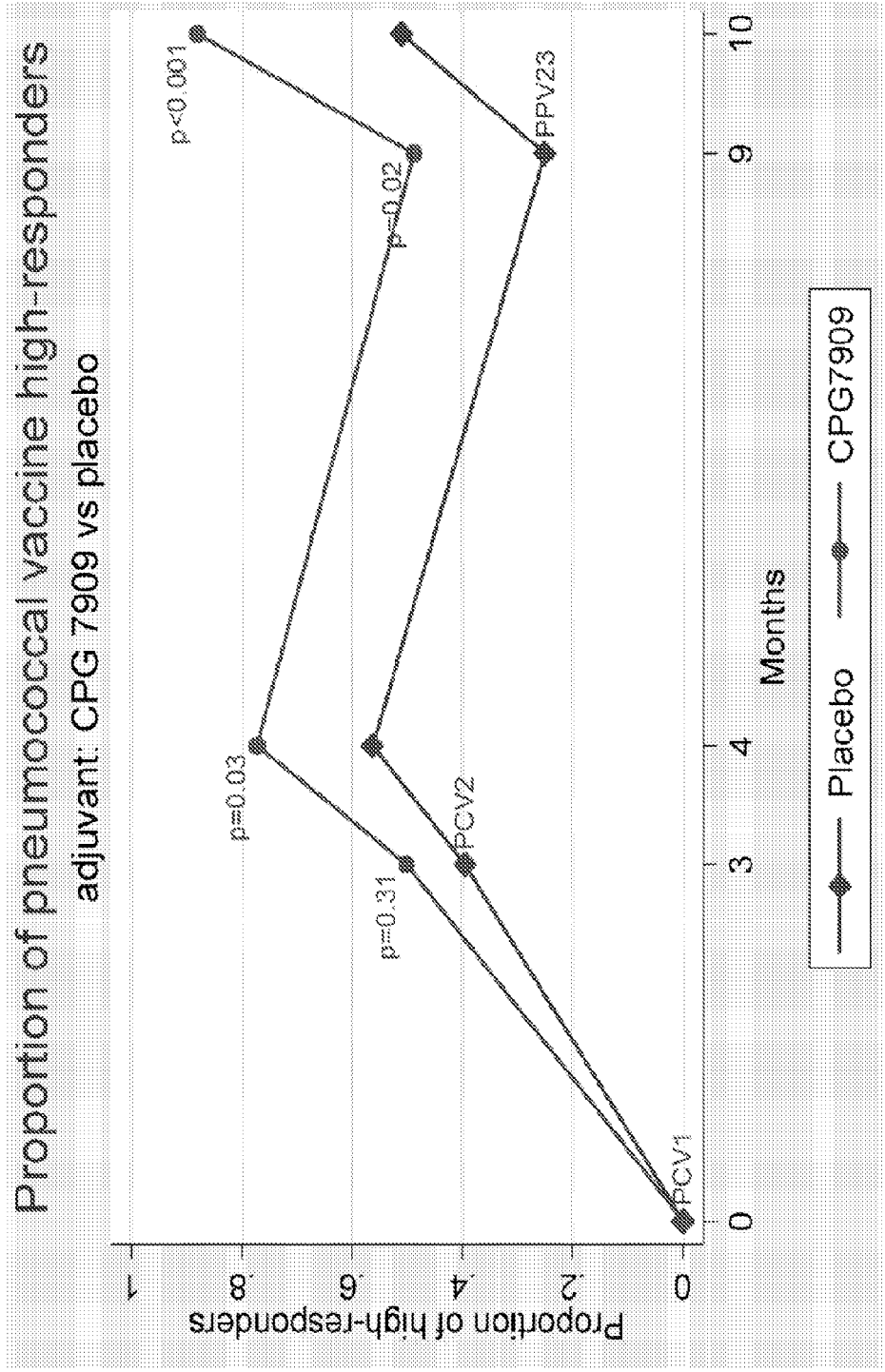
FIG. 1 shows the proportion of pneumococcal vaccine high-responders in the CPG-7909 group compared to the placebo group.

In an embodiment of the present invention, a TLR-9 agonist for use in the present invention is a CpG Oligonucleotide. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

Different classes of CpG immunostimulatory oligonucleotides have been identified. These are referred to as A, B, C and P class, and are described in greater detail below. Methods of the invention embrace the use of these different classes of CpG immunostimulatory oligonucleotides.

Any of the classes may be subjugated to an E modification which enhances its potency. An E modification may be a halogen substitution for the 5' terminal nucleotide; examples of such substitutions include but are not limited to bromo-uridine or iodo-uridine substitutions. An E modification can also include an ethyl-uridine substituation for the 5' terminal nucleotide.

The "A class" CpG immunostimulatory oligonucleotides are characterized functionally by the ability to induce high levels of interferon-alpha (IFN-α) from plasmacytoid dendritic cells (pDC) and inducing NK cell activation while having minimal effects on B cell activation. Structurally, this class typically has stabilized poly-G sequences at 5' and 3' ends. It also has a palindromic phosphodiester CpG dinucleotide-containing sequence of at least 6 nucleotides, for example but not necessarily, it contains one of the following hexamer palindromes: GACGTC, AGCGCT, or AACGTT described by Yamamoto and colleagues. Yamamoto S et al. J. Immunol 148:4072-6 (1992). A class CpG immunostimulatory oligonucleotides and exemplary sequences of this class have been described in U.S. Non-Provisional patent application Ser. No. 09/672,126 and published PCT application PCT/USO0/26527 (WO 01/22990), both filed on Sep. 27, 2000.

In an embodiment, the "A class" CpG oligonucleotide of the invention has the following nucleic acid sequence: 5' GGGGACGACGTCGTGGGGGGG 3' (SEQ ID NO: 1)

Some non-limiting examples of A-Class oligonucleotides include: 5' G*G*G_G_A_C_G_A_C_G_T_C_G_T_G_G*G*G*G*G*G 3' (SEQ ID NO: 2); wherein * refers to a phosphorothioate bond and _ refers to a phosphodiester bond.

The "B class" CpG immunostimulatory oligonucleotides are characterized functionally by the ability to activate B cells and pDC except are relatively weak in inducing IFN-α and NK cell activation. Structurally, this class typically may be fully stabilized with phosphorothioate linkages, but it may also have one or more phosphodiester linkages, preferably between the cytosine and guanine of the CpG motif(s), in which case the molecule is referred to as semi-soft. In one embodiment, the TLR-9 agonist for use in the present invention is a B class CpG oligonucleotide represented by at least the formula: 5' $X_1X_2CGX_3X_4$ 3', wherein X1, X2, X3, and X4 are nucleotides. In one embodiment, $X_2$ is adenine, guanine, or thymine. In another embodiment, $X_3$ is cytosine, adenine, or thymine.

In another embodiment, the TLR-9 agonist for use in the present invention is a B class CpG oligonucleotide represented by at least the formula:

5' $N_1X_1X_2CGX_3X_4N_2$ 3', wherein $X_1$, $X_2$, $X_3$, and $X_4$ are nucleotides and N is any nucleotide and $N_1$ and $N_2$ are nucleic acid sequences composed of from about 0-25 N's each. In one embodiment, $X_1X_2$ is a dinucleotide selected from the group consisting of GpT, GpG, GpA, ApA, ApT, ApG, CpT, CpA, CpG, TpA, TpT and TpG; and $X_3X_4$ is a dinucleotide selected from the group consisting of TpT, ApT, TpG, ApG, CpG, TpC, ApC, CpC, TpA, ApA and CpA. Preferably $X_1X_2$ is GpA or GpT and X3X4 is TpT. In other embodiments, $X_1$ or $X_2$ or both are purines and $X_3$ or $X_4$ or both are pyrimidines or $X_1X_2$ is GpA and $X_3$ or $X_4$ or both are pyrimidines. In one preferred embodiment, $X_1X_2$ is a dinucleotide selected from the group consisting of TpA, ApA, ApC, ApG and GpG. In yet another embodiment, $X_3X_4$ is a dinucleotide selected from the group consisting of TpT, TpA, TpG, ApA, ApG, GpA and CpA. $X_1X_2$, in another embodiment, is a dinucleotide selected from the group consisting of TpT, TpG, ApT, GpC, CpC, CpT, TpC, GpT and CpG; $X_3$ is a nucleotide selected from the group consisting of A and T, and $X_4$ is a nucleotide, but when $X_1X_2$ is TpC, GpT or CpG, $X_3X_4$ is not TpC, ApT or ApC.

In another preferred embodiment, the CpG oligonucleotide has the sequence 5' TCN$_1$TX$_1$X$_2$CGX$_3$X$_4$ 3'. The CpG oligonucleotides of the invention, in some embodiments, include $X_1X_2$ selected from the group consisting of GpT, GpG, GpA and ApA and X3X4 selected from the group consisting of TpT, CpT and TpC.

The B class CpG oligonucleotide sequences of the invention are those broadly described above as well as disclosed in published PCT Patent Applications PCT/US95/01570 and PCT/US97/19791, and in U.S. Pat. Nos. 6,194,388, 6,207, 646, 6,214,806, 6,218,371, 6,239,116 and 6,339,068. Exemplary sequences include but are not limited to those disclosed in these latter applications and patents.

In an embodiment, the "B class" CpG oligonucleotide of the invention has the following nucleic acid sequence:

```
                                       (SEQ ID NO: 3)
5' TCGTCGTTTTTCGGTGCTTTT 3',
or
                                       (SEQ ID NO: 4)
5' TCGTCGTTTTTCGGTCGTTTT 3',
or
                                       (SEQ ID NO: 5)
5' TCGTCGTTTTGTCGTTTTGTCGTT 3',
or
                                       (SEQ ID NO: 6)
5' TCGTCGTTTCGTCGTTTTGTCGTT 3',
or
                                       (SEQ ID NO: 7)
5' TCGTCGTTTTGTCGTTTTTTTCGA 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

Some non-limiting examples of B-Class oligonucleotides include:

```
                                       (SEQ ID NO: 8)
5' T*C*G*T*C*G*T*T*T*T*T*C*G*G*T*G*C*T*T*T*T 3',
or
                                       (SEQ ID NO: 9)
5' T*C*G*T*C*G*T*T*T*T*T*C*G*G*T*C*G*T*T*T*T 3',
or
                                       (SEQ ID NO: 10)
5' T*C*G*T*C*G*T*T*T*T*G*T*C*G*T*T*T*T*G*T*C*G*T*
T 3',
or
                                       (SEQ ID NO: 11)
5' T*C*G*T*C*G*T*T*T*C*G*T*C*G*T*T*T*T*G*T*C*G*T*
T 3',
or
                                       (SEQ ID NO: 12)
5' T*C*G*T*C*G*T*T*T*T*G*T*C*G*T*T*T*T*T*T*C*G*
A 3'.
``` wherein * refers to a phosphorothioate bond.

The "C class" of CpG immunostimulatory oligonucleotides is characterized functionally by the ability to activate B cells and NK cells and induce IFN-α. Structurally, this class typically includes a region with one or more B class-type immunostimulatory CpG motifs, and a GC-rich palindrome or near-palindrome region that allows the molecules to form secondary (e.g., stem-loop) or tertiary (e.g., dimer) type structures. Some of these oligonucleotides have both a traditional "stimulatory" CpG sequence and a "GC-rich" or "B-cell neutralizing" motif. These combination motif oligonucleotides have immune stimulating effects that fall somewhere between the effects associated with traditional B class CpG oligonucleotides (i.e., strong induction of B cell activation and dendritic cell (DC) activation), and the effects associated with A class CpG ODN (i.e., strong induction of IFN-α and NK cell activation but relatively poor induction of B cell and DC activation). Krieg A M et al. (1995) Nature 374:546-9; Bellas Z K et al. (1996) J Immunol 157:1840-5; Yamamoto S et al. (1992) J Immunol 148:4072-6.

The C class of combination motif immune stimulatory oligonucleotides may have either completely stabilized, (e.g., all phosphorothioate), chimeric (phosphodiester central region), or semi-soft (e.g., phosphodiester within CpG motif) backbones. This class has been described in U.S. patent application Ser. No. 10/224,523 filed on Aug. 19, 2002.

One stimulatory domain or motif of the C class CpG oligonucleotide is defined by the formula: 5' $X_1$DCGH$X_2$ 3'. D is a nucleotide other than C. C is cytosine. G is guanine. H is a nucleotide other than G. $X_1$ and $X_2$ are any nucleic acid sequence 0 to 10 nucleotides long. $X_1$ may include a CG, in which case there is preferably a T immediately preceding this CG. In some embodiments, DCG is TCG. $X_1$ is preferably from 0 to 6 nucleotides in length. In some embodiments, $X_2$ does not contain any poly G or poly A motifs. In other embodiments, the immunostimulatory oligonucleotide has a poly-T sequence at the 5' end or at the 3' end. As used herein, "poly-A" or "poly-T" shall refer to a stretch of four or more consecutive A's or T's respectively, e.g., 5' AAAA 3' or 5' TTTT 3'. As used herein, "poly-G end" shall refer to a stretch of four or more consecutive G's, e.g., 5' GGGG 3', occurring at the 5' end or the 3' end of a nucleic acid. As used herein, "poly-G oligonucleotide" shall refer to an oligonucleotide having the formula 5' $X_1X_2$GGG$X_3X_4$ 3' wherein $X_1$, $X_2$, $X_3$, and $X_4$ are nucleotides and preferably at least one of $X_3$ and $X_4$ is a G. Some preferred designs for the B cell stimulatory domain under this formula comprise TTTTTCG, TCG, TTCG, TTTCG, TTTTCG, TCGT, TTCGT, TTTCGT, TCGTCGT.

The second motif of the C class CpG oligonucleotide is referred to as either P or N and is positioned immediately 5' to $X_1$ or immediately 3' to $X_2$.

N is a B cell neutralizing sequence that begins with a CGG trinucleotide and is at least 10 nucleotides long. A B cell neutralizing motif includes at least one CpG sequence in which the CG is preceded by a C or followed by a G (Krieg A M et al. (1998) Proc Natl Acad Sd USA 95:12631-12636) or is a CG containing DNA sequence in which the C of the CG is methylated. Neutralizing motifs or sequences have some degree of immunostimulatory capability when present in an otherwise non-stimulatory motif, but when present in the context of other immunostimulatory motifs serve to reduce the immunostimulatory potential of the other motifs.

P is a GC-rich palindrome containing sequence at least 10 nucleotides long.

As used herein, "palindrome" and equivalently "palindromic sequence" shall refer to an inverted repeat, i.e., a sequence such as ABCDEE'D'C'B'A' in which A and A', B and B', etc., are bases capable of forming the usual Watson-Crick base pairs.

As used herein, "GC-rich palindrome" shall refer to a palindrome having a base composition of at least two-thirds G's and Cs. In some embodiments the GC-rich domain is preferably 3' to the "B cell stimulatory domain". In the case of a 10-base long GC-rich palindrome, the palindrome thus contains at least 8 G's and Cs. In the case of a 12-base long GC-rich palindrome, the palindrome also contains at least 8 G's and Cs. In the case of a 14-mer GC-rich palindrome, at least ten bases of the palindrome are G's and Cs. In some embodiments the GC-rich palindrome is made up exclusively of G's and Cs. In some embodiments the GC-rich palindrome has a base composition of at least 81% G's and Cs. In the case of such a 10-base long GC-rich palindrome, the palindrome thus is made exclusively of G's and Cs. In the case of such a 12-base long GC-rich palindrome, it is preferred that at least ten bases (83%) of the palindrome are G's and Cs. In some preferred embodiments, a 12-base long GC-rich palindrome is made exclusively of G's and Cs. In the case of a 14-mer GC-rich palindrome, at least twelve bases (86%) of the palindrome are G's and Cs. In some preferred embodiments, a 14-base long GC-rich palindrome is made exclusively of G's and Cs. The Cs of a GC-rich palindrome can be unmethylated or they can be methylated.

In general this domain has at least 3 Cs and Gs, more preferably 4 of each, and most preferably 5 or more of each. The number of Cs and Gs in this domain need not be identical. It is preferred that the Cs and Gs are arranged so that they are able to form a self-complementary duplex, or palindrome, such as CCGCGCGG. This may be interrupted by As or Ts, but it is preferred that the self-complementarity is at least partially preserved as for example in the motifs CGACGT-TCGTCG or CGGCGCCGTGCCG. When complementarity is not preserved, it is preferred that the non-complementary base pairs be TG. In a preferred embodiment there are no more than 3 consecutive bases that are not part of the palindrome, preferably no more than 2, and most preferably only 1. In some embodiments, the GC-rich palindrome includes at least one CGG trimer, at least one CCG trimer, or at least one CGCG tetramer. In other embodiments, the GC-rich palindrome is not CCCCCCGGGGGG or GGGGGGCCCCCC, CCCCCGGGGG or GGGGGCCCCC.

At least one of the G's of the GC rich region may be substituted with an inosine (I). In some embodiments, P includes more than one I.

In certain embodiments, the immunostimulatory oligonucleotide has one of the following formulas 5' NX$_1$DCGHX$_2$ 3', 5' X$_1$DCGHX$_2$N 3', 5' PX$_1$DCGHX$_2$ 3', 5' X$_1$DCGHX$_2$P 3', 5' X$_1$DCGHX$_2$PX$_3$ 3', 5' X$_1$DCGHPX$_3$ 3', 5' DCGHX$_2$PX$_3$ 3', 5' TCGHX$_2$PX$_3$ 3', 5' DCGHPX$_3$ 3' or 5'DCGHP 3'.

The invention provides other immune stimulatory oligonucleotides defined by a formula 5' N$_1$PyGN$_2$P 3'. N$_1$ is any sequence 1 to 6 nucleotides long. Py is a pyrimidine. G is guanine. N$_2$ is any sequence 0 to 30 nucleotides long. P is a GC-rich palindrome containing a sequence at least 10 nucleotides long.

N$_1$ and N$_2$ may contain more than 50% pyrimidines, and more preferably more than 50% T. N$_1$ may include a CG, in which case there is preferably a T immediately preceding this CG. In some embodiments, N1PyG is TCG, and most preferably a TCGN$_2$, where N$_2$ is not G. N$_1$PyGN$_2$P may include one or more inosine (I) nucleotides. Either the C or the G in N$_1$ may be replaced by inosine, but the CpI is preferred to the IpG. For inosine substitutions such as IpG, the optimal activity may be achieved with the use of a "semi-soft" or chimeric backbone, where the linkage between the IG or the CI is phosphodiester. N1 may include at least one CI, TCI, IG or TIG motif.

In certain embodiments N$_1$PyGN$_2$ is a sequence selected from the group consisting of TTTTTCG, TCG, TTCG, TTTCG, TTTTCG, TCGT, TTCGT, TTTCGT, and TCGTCGT.

In an embodiment, the "C class" CpG oligonucleotides of the invention has the following nucleic acid sequence:

```
                                    (SEQ ID NO: 13)
5' TCGCGTCGTTCGGCGCGCGCCG 3',
or
                                    (SEQ ID NO: 14)
5' TCGTCGACGTTCGGCGCGCGCCG 3',
or
                                    (SEQ ID NO: 15)
5' TCGGACGTTCGGCGCGCGCCG 3',
or
                                    (SEQ ID NO: 16)
5' TCGGACGTTCGGCGCGCCG 3',
or
                                    (SEQ ID NO: 17)
5' TCGCGTCGTTCGGCGCGCCG 3',
or
                                    (SEQ ID NO: 18)
5' TCGACGTTCGGCGCGCGCCG 3',
or
                                    (SEQ ID NO: 19)
5' TCGACGTTCGGCGCGCCG 3',
or
                                    (SEQ ID NO: 20)
5' TCGCGTCGTTCGGCGCCG 3',
or
                                    (SEQ ID NO: 21)
5' TCGCGACGTTCGGCGCGCGCCG 3',
or
                                    (SEQ ID NO: 22)
5' TCGTCGTTTTCGGCGCGCGCCG 3',
or
                                    (SEQ ID NO: 23)
5' TCGTCGTTTTCGGCGGCCGCCG 3',
or
                                    (SEQ ID NO: 24)
5' TCGTCGTTTTACGGCGCCGTGCCG 3',
or
                                    (SEQ ID NO: 25)
5' TCGTCGTTTTCGGCGCGCGCCGT 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide.

Some non-limiting examples of C-Class oligonucleotides include:

```
                                              (SEQ ID NO: 26)
5' T*C_G*C_G*T*C_G*T*T*C_G*G*C*G*C_G*C*G*C*C*G 3',
or
                                              (SEQ ID NO: 27)
5' T*C_G*T*C_G*A*C_G*T*T*C_G*G*C*G*C_G*C*G*C*C*
G 3',
or
                                              (SEQ ID NO: 28)
5' T*C_G*G*A*C_G*T*T*C_G*G*C*G*C_G*C*G*C*C*G 3',
or
                                              (SEQ ID NO: 29)
5' T*C_G*G*A*C_G*T*T*C_G*G*C*G*C*G*C*C*G 3',
or
                                              (SEQ ID NO: 30)
5' T*C_G*C_G*T*C_G*T*T*C_G*G*C*G*C*G*C*C*G 3',
or
                                              (SEQ ID NO: 31)
5' T*C_G*A*C_G*T*T*C_G*G*C*G*C_G*C*G*C*C*G 3',
or
                                              (SEQ ID NO: 32)
5' T*C_G*A*C_G*T*T*C_G*G*C*G*C*G*C*C*G 3',
or
                                              (SEQ ID NO: 33)
5' T*C_G*C_G*T*C_G*T*T*C_G*G*C*G*C*G*C*C*G 3',
or
                                              (SEQ ID NO: 34)
5' T*C_G*C_G*A*C_G*T*T*C_G*G*C*G*C_G*C*G*C*C*G 3',
or
                                              (SEQ ID NO: 35)
5' T*C*G*T*C*G*T*T*T*T*C*G*G*C*G*C*G*C*G*C*C*G 3',
or
                                              (SEQ ID NO: 36)
5' T*C*G*T*C*G*T*T*T*T*C*G*G*C*G*G*C*C*G*C*C*G 3',
or
                                              (SEQ ID NO: 37)
5' T*C*G*T*C_G*T*T*T*T*A*C_G*G*C*G*C*C_G*T*G*C*C*
G 3',
or
                                              (SEQ ID NO: 38)
5' T*C_G*T*C*G*T*T*T*T*C*G*G*C*G*C*G*C*G*C*C*G*
T 3'
``` wherein * refers to a phosphorothioate bond and _ refers to a phosphodiester bond.

In any of these sequences, an ethyl-uridine or a halogen may substitute for the 5' T; examples of halogen substitutions include but are not limited to bromo-uridine or iodo-uridine substitutions.

The "P class" CpG immunostimulatory oligonucleotides have been described in WO2007/095316 and are characterized by the fact that they contain duplex forming regions such as, for example, perfect or imperfect palindromes at or near both the 5' and 3' ends, giving them the potential to form higher ordered structures such as concatamers. These oligonucleotides referred to as P-Class oligonucleotides have the ability in some instances to induce much high levels of IFN-α secretion than the C-Class. The P-Class oligonucleotides have the ability to spontaneously self-assemble into concatamers either in vitro and/or in vivo. Without being bound by any particular theory for the method of action of these molecules, one potential hypothesis is that this property endows the P-Class oligonucleotides with the ability to more highly crosslink TLR9 inside certain immune cells, inducing a distinct pattern of immune activation compared to the previously described classes of CpG oligonucleotides.

In an embodiment, the TLR-9 agonist for use in the present invention is a P class CpG oligonucleotide containing a 5' TLR activation domain and at least two palindromic regions, one palindromic region being a 5' palindromic region of at least 6 nucleotides in length and connected to a 3' palindromic region of at least 8 nucleotides in length either directly or through a spacer, wherein the oligonucleotide includes at least one YpR dinucleotide. In an embodiment, said oligonucleotide is not T*C_G*T*C_G*A*C_G*T*T*C_G*G*C*G*C_G*C*G*C*C*G (SEQ ID NO: 27). In one embodiment the a P class CpG oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT. In yet another embodiment the TLR activation domain is within the 5' palindromic region. In another embodiment the TLR activation domain is immediately 5' to the 5' palindromic region. In still another embodiment the 5' palindromic region is at least 8 nucleotides in length. In another embodiment the 3' palindromic region is at least 10 nucleotides in length. In another embodiment the 5' palindromic region is at least 10 nucleotides in length. In yet another embodiment the 3' palindromic region includes an unmethylated CpG dinucleotide. In another embodiment the 3' palindromic region includes two unmethylated CpG dinucleotides. In another embodiment the 5' palindromic region includes an unmethylated CpG dinucleotide. In yet another embodiment the 5' palindromic region includes two unmethylated CpG dinucleotides. In another embodiment the 5' and 3' palindromic regions have a duplex stability value of at least 25. In another embodiment the 5' and 3' palindromic regions have a duplex stability value of at least 30. In another embodiment the 5' and 3' palindromic regions have a duplex stability value of at least 35. In another embodiment the 5' and 3' palindromic regions have a duplex stability value of at least 40. In another embodiment the 5' and 3' palindromic regions have a duplex stability value of at least 45. In another embodiment the 5' and 3' palindromic regions have a duplex stability value of at least 50. In another embodiment the 5' and 3' palindromic regions have a duplex stability value of at least 55. In another embodiment the 5' and 3' palindromic regions have a duplex stability value of at least 60. In another embodiment the 5' and 3' palindromic regions have a duplex stability value of at least 65.

In one embodiment the two palindromic regions are connected directly. In another embodiment the two palindromic regions are connected via a 3'-3' linkage. In another embodiment the two palindromic regions overlap by one nucleotide. In yet another embodiment the two palindromic regions overlap by two nucleotides. In another embodiment the two palindromic regions do not overlap. In another embodiment the two palindromic regions are connected by a spacer. In one embodiment the spacer is a nucleic acid having a length of 1-50 nucleotides. In another embodiment the spacer is a nucleic acid having a length of 1 nucleotide. In another embodiment the spacer is a non-nucleotide spacer. In one embodiment the non-nucleotide spacer is a D-spacer. In another embodiment the non-nucleotide spacer is a linker. In one embodiment the oligonucleotide has the formula 5' $XP_1SP_2T$ 3', wherein X is the TLR activation domain, $P_1$ is a palindrome, S is a spacer, $P_2$ is a palindrome, and T is a 3' tail of 0-100 nucleotides in length. In one embodiment X is TCG, TTCG, or TTTCG. In another embodiment T is 5-50 nucleotides in length. In yet another embodiment T is 5-10 nucleotides in length. In one embodiment S is a nucleic acid having a length of 1-50 nucleotides. In another embodiment S is a nucleic acid having a length of 1 nucleotide. In another embodiment S is a non-nucleotide spacer. In one embodiment the non-nucleotide spacer is a D-spacer. In another embodiment the non-nucleotide spacer is a linker. In another embodiment the oligonucleotide is not an antisense oligonucleotide or a ribozyme. In one embodiment $P_1$ is A and T rich. In another embodiment $P_1$ includes at least 4 Ts. In another embodiment $P_2$ is a perfect palindrome. In another embodiment P2 is G-C rich. In still another embodiment $P_2$ is $CGGCGCX_1GCGCCG$, where $X_1$ is T or nothing.

In one embodiment the oligonucleotide includes at least one phosphorothioate linkage. In another embodiment all internucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, the TLR-9 agonist for use in the present invention is a P class CpG oligonucleotide with a 5' TLR activation domain and at least two complementarity-containing regions, a 5' and a 3' complementarity-containing region, each complementarity-containing region being at least 8 nucleotides in length and connected to one another either directly or through a spacer, wherein the oligonucleotide includes at least one pyrimidine-purine (YpR) dinucleotide, and wherein at least one of the complementarity-containing regions is not a perfect palindrome. In one embodiment the oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT. In another embodiment the TLR activation domain is within the 5' complementarity-containing region. In another embodiment the TLR activation domain is immediately 5' to the 5' complementarity-containing region. In another embodiment the 3' complementarity-containing region is at least 10 nucleotides in length. In yet another embodiment the 5' complementarity-containing region is at least 10 nucleotides in length. In one embodiment the 3' complementarity-containing region includes an unmethylated CpG dinucleotide. In another embodiment the 3' complementarity-containing region includes two unmethylated CpG dinucleotides. In yet another embodiment the 5' complementarity-containing region includes an unmethylated CpG dinucleotide. In another embodiment the 5' complementarity-containing region includes two unmethylated CpG dinucleotides. In another embodiment the complementarity-containing regions include at least one nucleotide analog. In another embodiment the complementarity-containing regions form an intramolecular duplex. In one embodiment the intramolecular duplex includes at least one non-Watson Crick base pair. In another embodiment the non-Watson Crick base pair is G-T, G-A, G-G, or C-A. In one embodiment the complementarity-containing regions form intermolecular duplexes. In another embodiment at least one of the intermolecular duplexes includes at least one non-Watson Crick base pair. In another embodiment the non-Watson Crick base pair is G-T, G-A, G-G, or C-A. In yet another embodiment the complementarity-containing regions contain a mismatch. In still another embodiment the complementarity-containing regions contain two mismatches. In another embodiment the complementarity-containing regions contain an intervening nucleotide. In another embodiment the complementarity-containing regions contain two intervening nucleotides.

In one embodiment the 5' and 3' complementarity-containing regions have a duplex stability value of at least 25. In another embodiment the 5' and 3' complementarity-containing regions have a duplex stability value of at least 30. In another embodiment the 5' and 3' complementarity-containing regions have a duplex stability value of at least 35. In another embodiment the complementarity-containing regions have a duplex stability value of at least 40. In another embodiment the complementarity-containing regions have a duplex stability value of at least 45. In another embodiment the complementarity-containing regions have a duplex stability value of at least 50. In another embodiment the complementarity-containing regions have a duplex stability value of at least 55. In another embodiment the complementarity-containing regions have a duplex stability value of at least 60. In another embodiment the complementarity-containing regions have a duplex stability value of at least 65.

In another embodiment the two complementarity-containing regions are connected directly. In another embodiment the two palindromic regions are connected via a 3'-3' linkage. In yet another embodiment the two complementarity-containing regions overlap by one nucleotide. In another embodiment the two complementarity-containing regions overlap by two nucleotides. In another embodiment the two complementarity-containing regions do not overlap. In another embodiment the two complementarity-containing regions are connected by a spacer. In another embodiment the spacer is a nucleic acid having a length of 1-50 nucleotides. In another embodiment the spacer is a nucleic acid having a length of 1 nucleotide. In one embodiment the spacer is a non-nucleotide spacer. In another embodiment the non-nucleotide spacer is a D-spacer. In yet another embodiment the non-nucleotide spacer is a linker.

In one embodiment the P-class oligonucleotide has the formula 5' XNSPT 3', wherein X is the TLR activation domain, N is a non-perfect palindrome, P is a palindrome, S is a spacer, and T is a 3' tail of 0-100 nucleotides in length. In another embodiment X is TCG, TTCG, or TTTCG. In another embodiment T is 5-50 nucleotides in length. In another embodiment T is 5-10 nucleotides in length. In another embodiment S is a nucleic acid having a length of 1-50 nucleotides. In another embodiment S is a nucleic acid having a length of 1 nucleotide. In another embodiment S is a non-nucleotide spacer. In another embodiment the non-nucleotide spacer is a D-spacer. In another embodiment the non-nucleotide spacer is a linker. In another embodiment the oligonucleotide is not an antisense oligonucleotide or a ribozyme. In another embodiment N is A and T rich. In another embodiment N is includes at least 4 Ts. In another embodiment P is a perfect palindrome. In another embodiment P is G-C rich. In another embodiment P is $CGGCGCX_1GCGCCG$, wherein $X_1$ is T or nothing. In another embodiment the oligonucleotide includes at least one phosphorothioate linkage. In another embodiment all interaucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, the "P class" CpG oligonucleotides of the invention has the following nucleic acid sequence: 5' TCGTCGACGATCGGCGCGCGCCG 3' (SEQ ID NO: 39).

In said sequences, all of the linkages may be all phosphorothioate bonds. In another embodiment, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

A non-limiting example of P-Class oligonucleotides include:

```
                                            (SEQ ID NO: 40)
5' T*C_G*T*C_G*A*C_G*A*T*C_G*G*C*G*C_G*C*G*C*C*G 3'
``` wherein * refers to a phosphorothioate bond and _ refers to a phosphodiester bond.

In an embodiment, all the internucleotide linkage of the CpG oligonucleotides disclosed herein are phosphodiester bonds ("soft" oligonucleotides, as described in the PCT application WO2007/026190). In another embodiment, CpG oligonucleotides of the invention are rendered resistant to degradation (e.g., are stabilized). A "stabilized oligonucleotide" refers to an oligonucleotide that is relatively resistant to in vivo degradation (e.g. via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases.

The immunostimulatory oligonucleotides may have a chimeric backbone, which have combinations of phosphodiester and phosphorothioate linkages. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. When the phosphodiester linkage is preferentially located within the CpG motif such molecules are called "semi-soft" as described in the PCT application WO2007/026190.

Other modified oligonucleotides include combinations of phosphodiester, phosphorothioate, methylphosphonate, methyl phosphorothioate, phosphorodithioate, and/or p-ethoxy linkages.

Since boranophosphonate linkages have been reported to be stabilized relative to phosphodiester linkages, for purposes of the chimeric nature of the backbone, boranophosphonate linkages can be classified either as phosphodiester-like or as stabilized, depending on the context. For example, a chimeric backbone according to the instant invention could, in some embodiments, includes at least one phosphodiester (phosphodiester or phosphodiester-like) linkage and at least one boranophosphonate (stabilized) linkage. In other embodiments, a chimeric backbone according to the instant invention could include boranophosphonate (phosphodiester or phosphodiester-like) and phosphorothioate (stabilized) linkages. A "stabilized internucleotide linkage" shall mean an internucleotide linkage that is relatively resistant to in vivo degradation (e.g., via an exo- or endo-nuclease), compared to a phosphodiester internucleotide linkage. Preferred stabilized internucleotide linkages include, without limitation, phosphorothioate, phosphorodithioate, methylphosphonate, and methyl phosphorothioate. Other stabilized internucleotide linkages include, without limitation, peptide, alkyl, dephospho, and others as described above.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165. Methods for preparing chimeric oligonucleotides are also known. For instance patents issued to Uhlmann et al have described such techniques.

Mixed backbone modified ODN may be synthesized as described in the PCT application WO2007/026190.

The oligonucleotides of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The size of the CpG oligonucleotide (i.e., the number of nucleotide residues along the length of the oligonucleotide) also may contribute to the stimulatory activity of the oligonucleotide. For facilitating uptake into cells, CpG oligonucleotide of the invention preferably have a minimum length of 6 nucleotide residues. Oligonucleotides of any size greater than 6 nucleotides (even many kb long) are capable of inducing an immune response if sufficient immunostimulatory motifs are present, because larger oligonucleotides are degraded inside cells. In certain embodiments, the CpG oligonucleotides are 6 to 100 nucleotides long, preferentially 8 to 30 nucleotides long. In important embodiments, nucleic acids and oligonucleotides of the invention are not plasmids or expression vectors.

In an embodiment, the CpG oligonucleotide disclosed herein comprise substitutions or modifications, such as in the bases and/or sugars as described at paragraph 134 to 147 of WO2007/026190.

In an embodiment, the CpG oligonucleotide of the present invention is chemically modified. Examples of chemical modifications are known to the skilled person and are described, for example in Uhlmann E. et al. (1990), Chem. Rev. 90:543, S. Agrawal, Ed., Humana Press, Totowa, USA 1993; Crooke, S. T. et al. (1996) Annu. Rev. Pharmacol. Toxicol. 36:107-129; and Hunziker J. et al., (1995), Mod. Synth. Methods 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

In some embodiments of the invention, CpG-containing nucleic acids might be simply mixed with immunogenic carriers according to methods known to those skilled in the art (see, e.g. WO03/024480).

In a particular embodiment of the present invention, any of the vaccine disclosed herein comprises from 2 µg to 100 mg of CpG oligonucleotide, preferably from 0.1 mg to 50 mg CpG oligonucleotide, preferably from 0.2 mg to 10 mg CpG oligonucleotide, preferably from 0.3 mg to 5 mg CpG oligonucleotide, preferably from 0.3 mg to 5 mg CpG oligonucleotide, even preferably from 0.5 to 2 mg CpG oligonucleotide, even preferably from 0.75 to 1.5 mg CpG oligonucleotide. In a preferred embodiment, any of the vaccine disclosed herein comprises approximately 1 mg CpG oligonucleotide.

Pneumococcal Vaccines

Pneumococcal vaccine of the present invention will typically comprise conjugated capsular saccharide antigens, wherein the saccharides are derived from at least seven serotypes of S. pneumoniae. The number of S. pneumoniae capsular saccharides can range from 7 different serotypes (or "v", valences) to 23 different serotypes (23v). In one embodiment there are 7, 8, 9, 10, 11, 12, 13, 14, 15, 16, 17, 18, 19, 20, 21, 22 or 23 different serotypes. In an embodiment there are 10 or 11 different serotypes. In an embodiment there are 7 or 13 different serotypes. The capsular saccharide antigens are conjugated to a carrier protein as described here below.

In another embodiment of the invention, the vaccine may comprise conjugated S. pneumoniae saccharides and unconjugated S. pneumoniae saccharides. Preferably, the total number of saccharide serotypes is less than or equal to 23. For example, the vaccine may comprise 7 conjugated serotypes and 16 unconjugated saccharides. In another embodiment, the vaccine may comprise 13 conjugated serotypes and 10 unconjugated saccharides. In a similar manner, the vaccine may comprise 8, 9, 10, 11, 12, 13, 14, 15 or 16 conjugated saccharides and 15, 14, 13, 12, 11, 10, 9, 8 or 7, respectively, unconjugated saccharides.

1. In an embodiment the vaccine of the invention comprises conjugated S. pneumoniae saccharides from serotypes 4, 6B, 9V, 14, 18C, 19F and. 23F.

2. In another embodiment the vaccine of the invention comprises in addition to point 1 above, conjugated S. pneumoniae saccharides from serotype 1.

3. In another embodiment the vaccine of the invention comprises in addition to point 1 or 2 above, conjugated S. pneumoniae saccharides from serotype 5.

4. In another embodiment the vaccine of the invention comprises in addition to point 1, 2 or 3 above, conjugated S. pneumoniae saccharides from serotype 7F.

5. In another embodiment the vaccine of the invention comprises in addition to point 1, 2, 3 or 4 above, conjugated S. pneumoniae saccharides from serotype 3.

6. In another embodiment the vaccine of the invention comprises in addition to point 1, 2, 3, 4 or 5 above, conjugated S. pneumoniae saccharides from serotype 6A.

7. In another embodiment the vaccine of the invention comprises in addition to point 1, 2, 3, 4, 5 or 6 above, conjugated S. pneumoniae saccharides from serotype 19A.

8. In another embodiment the vaccine of the invention comprises in addition to point 1, 2, 3, 4, 5, 6 or 7 above, conjugated S. pneumoniae saccharides from serotype 22F.

9. In another embodiment the vaccine of the invention comprises in addition to point 1, 2, 3, 4, 5, 6, 7 or 8 above, conjugated S. pneumoniae saccharides from serotype 15.

10. In another embodiment the vaccine of the invention comprises in addition to point 1, 2, 3, 4, 5, 6, 7, 8 or 9 above, conjugated S. pneumoniae saccharides from serotype 8.

11. In another embodiment the vaccine of the invention comprises in addition to point 1, 2, 3, 4, 5, 6, 7, 8, 9 or 10 above, conjugated S. pneumoniae saccharides from serotype 12F.

12. In another embodiment the vaccine of the invention comprises in addition to point 1, 2, 3, 4, 5, 6, 7, 8, 9, 10 or 11 above, conjugated S. pneumoniae saccharides from serotype 2.

13. In another embodiment the vaccine of the invention comprises in addition to point 1, 2, 3, 4, 5, 6, 7, 8, 9, 11 or 12 above, conjugated S. pneumoniae saccharides from serotype 9N.

14. In another embodiment the vaccine of the invention comprises in addition to point 1, 2, 3, 4, 5, 6, 7, 8, 9, 11, 12 or 13 above, conjugated S. pneumoniae saccharides from serotype 10A.

15. In another embodiment the vaccine of the invention comprises in addition to point 1, 2, 3, 4, 5, 6, 7, 8, 9, 11, 12, 13 or 14 above, conjugated S. pneumoniae saccharides from serotype 11A.

16. In another embodiment the vaccine of the invention comprises in addition to point 1, 2, 3, 4, 5, 6, 7, 8, 9, 11, 12, 13, 14, or 15 above, conjugated S. pneumoniae saccharides from serotype 11A.

17. In another embodiment the vaccine of the invention comprises in addition to point 1, 2, 3, 4, 5, 6, 7, 8, 9, 11, 12, 13, 14, 15 or 16 above, conjugated S. pneumoniae saccharides from serotype 17F.

18. In another embodiment the vaccine of the invention comprises in addition to point 1, 2, 3, 4, 5, 6, 7, 8, 9, 11, 12, 13, 14, 15, 16 or 17 above, conjugated S. pneumoniae saccharides from serotype 20.

19. In another embodiment the vaccine of the invention comprises in addition to point 1, 2, 3, 4, 5, 6, 7, 8, 9, 11, 12, 13, 14, 15, 16, 17 or 18 above, conjugated S. pneumoniae saccharides from serotype 33F.

In an embodiment the vaccine of the invention comprises conjugated S. pneumoniae saccharides from serotypes 4, 6B, 9V, 14, 18C, 19F and. 23F.

In an embodiment the vaccine of the invention comprises conjugated S. pneumoniae saccharides from serotypes 1, 3, 4, 5, 6A, 6B, 7F, 9V, 14, 18C, 19A, 19F and. 23F In an embodiment, the vaccine of the invention comprises conjugated S. pneumoniae saccharides from serotypes 1, 4, 5, 6B, 7F, 9V, 14, 18C, 19F and. 23F.

In an embodiment, the vaccine of the invention comprises conjugated S. pneumoniae saccharides from serotypes 1, 3, 4, 5, 6B, 7F, 9V, 14, 18C, 19F and 23F.

In a preferred embodiment, the capsular saccharide antigens are conjugated to a carrier protein independently selected from the group consisting of TT, DT, CRM197, fragment C of TT, PhtD, PhtDE fusions (particularly those described in WO 01/98334 and WO 03/54007), detoxified pneumolysin and protein D.

In a preferred embodiment, the capsular saccharide antigens are conjugated to a carrier proteins which is selected in the group consisting of: DT (Diphtheria toxin), TT (tetanus toxid) or fragment C of TT, CRM197 (a nontoxic but antigenically identical variant of diphtheria toxin) other DT point mutants, such as CRM176, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843, 711, pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE (sequences of PhtA, PhtB, PhtD or PhtE are disclosed in WO 00/37105 or WO 00/39299) and fusions of Pht proteins for example PhtDE fusions, PhtBE fusions, Pht A-E (WO 01/98334, WO 03/54007, WO2009/000826), OMPC (meningococcal outer membrane protein—usually extracted from N. meningitidis serogroup B—EP0372501), PorB (from N. meningitidis), PD (Haemophilus influenzae protein D—see, e.g., EP 0 594 610 B), or immunologically functional equivalents thereof, synthetic peptides (EP0378881, EP0427347), heat shock proteins (WO 93/17712, WO 94/03208), pertussis proteins (WO 98/58668, EP0471 177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of C. difficile (WO 00/61761).

In an embodiment, the capsular saccharide antigens are conjugated to DT (Diphtheria toxoid). In another embodiment, the capsular saccharide antigens are conjugated to TT (tetanus toxid).

In another embodiment, the capsular saccharide antigens are conjugated to fragment C of TT.

In another embodiment, the capsular saccharide antigens are conjugated to PD (Haemophilus influenzae protein D—see, e.g., EP 0 594 610 B).

In a preferred embodiment, the capsular saccharide antigens of the invention are conjugated to CRM197 protein. The CRM197 protein is a nontoxic form of diphtheria toxin but is immunologically indistinguishable from the diphtheria toxin. CRM197 is produced by C. diphtheriae infected by the non-toxigenic phage β197$^{tox-}$ created by nitrosoguanidine mutagenesis of the toxigenic corynephage beta (Uchida, T. et al. 1971, Nature New Biology 233:8-11). The CRM197 protein has the same molecular weight as the diphtheria toxin but differs therefrom by a single base change (guanine to adenine) in the structural gene. This single base change causes an amino acid substitution glutamic acid for glycine) in the mature protein and eliminates the toxic properties of diphtheria toxin. The CRM197 protein is a safe and effective T-cell dependent carrier for saccharides. Further details about CMR197 and production thereof can be found e.g. in U.S. Pat. No. 5,614,382.

In an embodiment, if the protein carrier is the same for 2 or more saccharides in the composition, the saccharides could be conjugated to the same molecule of the protein carrier (carrier molecules having 2 more different saccharides conjugated to it) [see for instance WO 04/083251].

Alternatively the saccharides may each be individually conjugated to different molecules of the protein carrier (each molecule of protein carrier only having one type of saccharide conjugated to it). In said embodiment, the capsular saccharides are said to be individually conjugated to the carrier protein.

In an embodiment, the capsular saccharide antigens of the present invention are from different S. pneumoniae serotypes and are conjugated to one or more carrier protein. In an embodiment the vaccine of the invention comprises 7, 8, 9, 10, 11, 12, 13, 14, 15, 16, 17, 18, 19, 20, 21, 22 or 23 different serotypes capsular saccharide conjugates in which CRM197 is the carrier protein.

In an embodiment the vaccine of the invention comprises 7, 8, 9, 10, 11, 12, 13, 14, 15, 16, 17, 18, 19, 20, 21, 22 or 23 different serotypes capsular saccharide conjugates in which protein D is the carrier protein.

In an embodiment, saccharide from serotype 1, 2, 3, 4, 5, 6B, 7F, 8, 9N, 9V, 10A, 11A, 12F, 14, 15B, 17F, 18C, 19A, 19F, 20, 22F, 23F or 33F is conjugated to protein D.

In an embodiment, saccharide from serotype 1, 2, 3, 4, 5, 6B, 7F, 8, 9N, 9V, 10A, 11A, 12F, 14, 15B, 17F, 18C, 19A, 19F, 20, 22F, 23F or 33F is conjugated to CRM197.

In an embodiment, saccharides from at least serotypes 1 and 3, 1 and 4, 1 and 5, 1 and 6A, 1 and 6B, 1 and 7, 1 and 9V, 1 and 14, 1 and 22F, 1 and 23F, 3 and 4, 3 and 5, 3 and 6A, 3 and 6B, 3 and 7F, 3 and 9V, 3 and 14, 3 and 22F, 3 and 23F, 4 and 5, 4 and 6A, 4 and 6B, 4 and 7F, 4 and 9V, 4 and 14, 4 and 22F, 4 and 23F, 5 and 6A, 5 and 6B, 5 and 7F, 5 and 9V, 5 and 14, 5 and 22F, 5 and 23F, 6A and 6B, 6A and 7F, 6A and 9V, 6A and 14, 6A and 22F, 6A and 23F, 6B and 7F, 6B and 9V, 6B and 14, 6B and 22F, 6B and 23F, 7F and 9V, 7F and 14, 7F and 22F, 7F and 23F, 9V and 14, 9V and 22F, 9V and 23F, 14 and 22F, 14 and 23F or 22F and 23F are conjugated to CRM197.

In an embodiment, saccharides from at least serotypes 1, 3 and 4; 1, 3 and 5; 1, 3 and 6A; 1, 3 and 6B; 1, 3 and 7F; 1, 3 and 9V; 1, 3 and 14; 3, 4 and 7F; 3, 4 and 5; 3, 4 and 7F; 3, 4 and 9V; 3, 4 and 14; 4, 5 and 7F; 4, 5 and 9V; 4, 5, and 14; 5, 7F and 9V; 5, 7F and 14; 7F, 9V and 14; 1, 3, 4 and 5; 3, 4, 5 and 7F; 4, 5, 7F and 9V; 4, 5, 7F and 14; 4, 5, 9V and 14; 4, 7F, 9V and 14; 5, 7F, 9V and 14; or 4, 5, 7F, 9V and 14 are conjugated to CRM197.

In an embodiment, saccharides from at least serotypes 1 and 3, 1 and 4, 1 and 5, 1 and 6A, 1 and 6B, 1 and 7, 1 and 9V, 1 and 14, 1 and 22F, 1 and 23F, 3 and 4, 3 and 5, 3 and 6A, 3 and 6B, 3 and 7F, 3 and 9V, 3 and 14, 3 and 22F, 3 and 23F, 4 and 5, 4 and 6A, 4 and 6B, 4 and 7F, 4 and 9V, 4 and 14, 4 and 22F, 4 and 23F, 5 and 6A, 5 and 6B, 5 and 7F, 5 and 9V, 5 and 14, 5 and 22F, 5 and 23F, 6A and 6B, 6A and 7F, 6A and 9V, 6A and 14, 6A and 22F, 6A and 23F, 6B and 7F, 6B and 9V, 6B and 14, 6B and 22F, 6B and 23F, 7F and 9V, 7F and 14, 7F and 22F, 7F and 23F, 9V and 14, 9V and 22F, 9V and 23F, 14 and 22F, 14 and 23F or 22F and 23F are conjugated to protein D.

In an embodiment, saccharides from at least serotypes 1, 3 and 4; 1, 3 and 5; 1, 3 and 6A; 1, 3 and 6B; 1, 3 and 7F; 1, 3 and 9V; 1, 3 and 14; 3, 4 and 7F; 3, 4 and 5; 3, 4 and 7F; 3, 4 and 9V; 3, 4 and 14; 4, 5 and 7F; 4, 5 and 9V; 4, 5, and 14; 5, 7F and 9V; 5, 7F and 14; 7F, 9V and 14; 1, 3, 4 and 5; 3, 4, 5 and 7F; 4, 5, 7F and 9V; 4, 5, 7F and 14; 4, 5, 9V and 14; 4, 7F, 9V and 14; 5, 7F, 9V and 14; or 4, 5, 7F, 9V and 14 are conjugated to protein D.

In an embodiment the vaccine of the invention comprises 7 different serotypes capsular saccharide conjugates in which CRM197 is the carrier protein.

In an embodiment the vaccine of the invention comprises 7 different serotypes capsular saccharide conjugates in which protein D is the carrier protein.

In an embodiment the vaccine of the invention comprises 10 different serotypes capsular saccharide conjugates in which CRM197 is the carrier protein.

In an embodiment the vaccine of the invention comprises 10 different serotypes capsular saccharide conjugates in which protein D is the carrier protein.

In an embodiment the vaccine of the invention comprises 11 different serotypes capsular saccharide conjugates in which CRM197 is the carrier protein.

In an embodiment the vaccine of the invention comprises 11 different serotypes capsular saccharide conjugates in which protein D is the carrier protein.

In an embodiment the vaccine of the invention comprises 13 different serotypes capsular saccharide conjugates in which CRM197 is the carrier protein.

In an embodiment the vaccine of the invention comprises 13 different serotypes capsular saccharide conjugates in which protein D is the carrier protein.

In an embodiment the vaccine of the invention comprises 23 different serotypes capsular saccharide conjugates in which CRM197 is the carrier protein.

In an embodiment the vaccine of the invention comprises 23 different serotypes capsular saccharide conjugates in which protein D is the carrier protein.

In an embodiment, the vaccine of the invention comprises saccharide from serotypes 4, 6B, 9V, 14, 18C, 19F and. 23F conjugated to protein D.

In an embodiment, the vaccine of the invention comprises saccharide from serotypes 4, 6B, 9V, 14, 18C, 19F and. 23F conjugated to CRM197.

In an embodiment, the vaccine of the invention comprises saccharide from serotypes 1, 3, 4, 5, 6A, 6B, 7F, 9V, 14, 18C, 19A, 19F and 23F conjugated to protein D.

In an embodiment, the vaccine of the invention comprises saccharide from serotypes 1, 3, 4, 5, 6A, 6B, 7F, 9V, 14, 18C, 19A, 19F and 23F conjugated to CRM197.

In an embodiment, the vaccine of the invention comprises saccharide from serotypes 1, 4, 5, 6B, 7F, 9V, 14, 18C, 19F and 23F conjugated to protein D.

In an embodiment, the vaccine of the invention comprises saccharide from serotypes 1, 4, 5, 6B, 7F, 9V, 14, 18C, 19F and 23F conjugated to CRM197.

In an embodiment, the vaccine of the invention comprises saccharide from serotypes 1, 3, 4, 5, 6B, 7F, 9V, 14, 18C, 19F and 23F conjugated to protein D.

In an embodiment, the vaccine of the invention comprises saccharide from serotypes 1, 3, 4, 5, 6B, 7F, 9V, 14, 18C, 19F and 23F conjugated to CRM197.

In an embodiment, the vaccine of the invention comprises saccharide from serotype 1, 2, 3, 4, 5, 6B, 7F, 8, 9N, 9V, 10A, 11A, 12F, 14, 15B, 17F, 18C, 19A, 19F, 20, 22F, 23F and 33F conjugated to protein D.

In an embodiment, the vaccine of the invention comprises saccharide from serotypes 1, 2, 3, 4, 5, 6B, 7F, 8, 9N, 9V, 10A, 11A, 12F, 14, 15B, 17F, 18C, 19A, 19F, 20, 22F, 23F and 33F conjugated to CRM197.

In an embodiment, the vaccine of the invention comprises saccharide from serotypes 1, 4, 5, 6B, 7F, 9V, 14, and 23F conjugated to protein D, saccharide from serotype 18C conjugated to tetanus toxoid (TT) and saccharide from serotype 19F conjugated to diphtheria toxoid (DT).

In an embodiment, the vaccine of the invention comprises saccharide from serotypes 1, 4, 5, 7F, 9V, 19F and 23F conjugated to tetanus toxoid (TT) and saccharide from serotypes 3, 14 18C and 6B conjugated to diphtheria toxoid (DT).

In an embodiment, the vaccine of the invention comprises saccharide from serotypes 1, 4, 5, 6B, 7F, 9V, 14, and 23F individually conjugated to protein D, saccharide from serotype 18C conjugated to tetanus toxoid (TT) and saccharide from serotype 19F conjugated to diphtheria toxoid (DT).

In an embodiment, the vaccine of the invention comprises saccharide from serotypes 1, 4, 5, 7F, 9V, 19F and 23F individually conjugated to tetanus toxoid (TT) and saccharide from serotypes 3, 14 18C and 6B conjugated to diphtheria toxoid (DT).

The term "saccharide" throughout this specification may indicate polysaccharide or oligosaccharide and includes both. Capsular polysaccharides of *Streptococcus pneumoniae* comprise repeating oligosaccharide units which may contain up to 8 sugar residues. For a review of the oligosaccharide units for the key *Streptococcus pneumoniae* serotypes see JONES, Christopher. Vaccines based on the cell surface carbohydrates of pathogenic bacteria. An. Acad. Bras. Cienc, June 2005, vol. 77, no. 2, p. 293-324. Table II ISSN 0001-3765.

Capsular saccharide antigens of the invention are prepared by standard techniques known to those skilled in the art. Typically polysaccharides conjugates are prepared by separate processes and formulated into a single dosage formulation. For example, in one embodiment, each pneumococcal polysaccharide serotype is grown in a soy-based medium. The individual polysaccharides are then purified through centrifugation, precipitation, ultra-filtration, and column chromatography. The purified polysaccharides are chemically activated to make the saccharides capable of reacting with the carrier protein. Once activated, each capsular polysaccharide is separately conjugated to a carrier protein to form a glycoconjugate. In one embodiment, each capsular polysaccharide is conjugated to the same carrier protein. In this embodiment, the conjugation is effected by reductive amination. The chemical activation of the polysaccharides and subsequent conjugation to the carrier protein are achieved by conventional means. See, for example, U.S. Pat. Nos. 4,673,574 and 4,902,506.

After conjugation of the capsular polysaccharide to the carrier protein, the polysaccharide-protein conjugates are purified (enriched with respect to the amount of polysaccharide-protein conjugate) by a variety of techniques. These techniques include concentration/diafiltration operations, precipitation/elution, column chromatography, and depth filtration. See for examples US2007/0184072 or WO2008/079653. After the individual glycoconjugates are purified, they are compounded to formulate the vaccine of the present invention. Formulation of the immunogenic composition of the present invention can be accomplished using art-recognized methods. For instance, the individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

The amount of conjugate in each vaccine dose is selected as an amount which induces an immunoprotective response without significant, adverse side effects in typical vaccines. Such amount will vary depending upon which specific immunogen is employed and how it is presented. In an embodiment, each dose comprises 0.1 to 1000 µg of each saccharide or saccharide-protein conjugate, preferably 2 to 100 µg, most preferably 4 to 40 µg.

In an embodiment, each dose comprises between 0.1 and 20 µg, 1 and 10 µg or 1 and 5 µg of saccharide.

In an embodiment, the vaccine of the invention contains each *S. pneumoniae* capsular saccharide at a dose of between 0.1-20 µg, 0.5-10 µg; 0.5-5 µg or 1-5 µg of saccharide. In an embodiment, capsular saccharides may be present at different dosages, for example some capsular saccharides may be present at a dose of around or exactly 2 µg or some capsular saccharides may be present at a dose of around or exactly 4 µg.

In a particular embodiment of the present invention, the vaccine contains saccharide from serotypes 4, 6B, 9V, 14, 18C, 19F and. 23F individually conjugated to CRM197 wherein each *S. pneumoniae* capsular saccharide is at a dose of 2 μg except for 6B which is at a dose of 4 μg.

In a particular embodiment of the present invention, the vaccine contains saccharide from serotypes 4, 6B, 9V, 14, 18C, 19F and 23F individually conjugated to CRM197 wherein each *S. pneumoniae* capsular saccharide is at a dose of 4 μg except for 6B which is at a dose of 8 μg.

In a particular embodiment of the present invention, the vaccine contains saccharide from serotypes 4, 6B, 9V, 14, 18C, 19F and 23F individually conjugated to CRM197 wherein each *S. pneumoniae* capsular saccharide is at a dose of 6 μg except for 6B which is at a dose of 12 μg.

In a particular embodiment of the present invention, the vaccine contains saccharide from serotypes 4, 6B, 9V, 14, 18C, 19F and. 23F individually conjugated to CRM197 wherein each *S. pneumoniae* capsular saccharide is at a dose of 8 μg except for 6B which is at a dose of 16 μg.

In a particular embodiment of the present invention, the vaccine contains saccharide from serotypes 1, 3, 4, 5, 6A, 6B, 7F, 9V, 14, 18C, 19A, 19F, and 23F individually conjugated to CRM197 wherein each *S. pneumoniae* capsular saccharide is at a dose of 2 μg except for 6B which is at a dose of 4 μg.

In a particular embodiment of the present invention, the vaccine contains saccharide from serotypes 1, 3, 4, 5, 6A, 6B, 7F, 9V, 14, 18C, 19A, 19F, and 23F individually conjugated to CRM197 wherein each *S. pneumoniae* capsular saccharide is at a dose of 4 μg except for 6B which is at a dose of 8 μg.

In a particular embodiment of the present invention, the vaccine contains saccharide from serotypes 1, 3, 4, 5, 6A, 6B, 7F, 9V, 14, 18C, 19A, 19F, and 23F individually conjugated to CRM197 wherein each *S. pneumoniae* capsular saccharide is at a dose of 6 μg except for 6B which is at a dose of 12 μg.

In a particular embodiment of the present invention, the vaccine contains saccharide from serotypes 1, 3, 4, 5, 6A, 6B, 7F, 9V, 14, 18C, 19A, 19F, and 23F individually conjugated to CRM197 wherein each *S. pneumoniae* capsular saccharide is at a dose of 8 μg except for 6B which is at a dose of 16 μg.

In a particular embodiment of the present invention, the vaccine disclosed herein contain from 5 to 500 μg, preferably 10 to 200 μg, even more preferably, 20 to 100 μg of CRM197 carrier protein.

In an embodiment of the present invention, the vaccine disclosed herein contain 20 to 50 μg, preferably 20 to 40 μg, even more preferably 25 to 30 μg, even more preferably approximately 28 or 29 μg of CRM197 carrier protein.

In an embodiment of the present invention, the vaccine disclosed herein contain 40 to 100 μg, preferably 40 to 80 μg, even more preferably 50 to 60 μg, even more preferably approximately 57 or 58 μg of CRM197 carrier protein.

In a particular embodiment of the present invention, the vaccine disclosed herein contain sodium chloride and/or sodium succinate buffer as excipients.

In an embodiment, the pneumococcal vaccine to be used herein is the 7-valent conjugated pneumococcal vaccine (Prevenar) or the 13-valent conjugated pneumococcal vaccine disclosed in US2007/0184072—Prevenar 13). 7-valent Prevenar contains saccharide from serotypes 4, 6B, 9V, 14, 18C, 19F and 23F individually conjugated to CRM197. 13-valent Prevenar contains saccharide from serotypes 1, 3, 4, 5, 6A, 6B, 7F, 9V, 14, 18C, 19A, 19F, and 23F individually conjugated to CRM197.

In an embodiment, the vaccine of the invention comprises saccharide from serotypes 1, 4, 5, 6B, 7F, 9V, 14, and 23F individually conjugated to protein D, saccharide from serotype 18C conjugated to tetanus toxoid (TT) and saccharide from serotype 19F conjugated to diphtheria toxoid (DT) wherein each *S. pneumoniae* capsular saccharide is at a dose of 1 μg except for 4, 18C and 19F which is at a dose of 3 μg. In a particular embodiment of the present invention, said vaccine contains from 5 to 500 μg, preferably 7 to 100 μg of protein D carrier protein, from 2 to 200 μg, preferably 4 to 50 μg of tetanus toxoid (TT) carrier protein and from 1 to 100 μg, preferably 2 to 25 μg of diphtheria toxoid (DT) carrier protein. In a particular embodiment of the present invention, said vaccine contains from 9 to 16 μg of protein D carrier protein, from 5 to 10 μg tetanus toxoid (TT) carrier protein and from 3 to 6 μg diphtheria toxoid (DT) carrier protein.

In an embodiment, the vaccine of the invention comprises saccharide from serotypes 1, 4, 5, 6B, 7F, 9V, 14, and 23F individually conjugated to protein D, saccharide from serotype 18C conjugated to tetanus toxoid (TT) and saccharide from serotype 19F conjugated to diphtheria toxoid (DT) wherein each *S. pneumoniae* capsular saccharide is at a dose of 2 μg except for 4, 18C and 19F which is at a dose of 6 μg. In a particular embodiment of the present invention, said vaccine contains from 10 to 1000 μg, preferably 14 to 200 μg of protein D carrier protein, from 4 to 400 μg, preferably 8 to 100 μg of tetanus toxoid (TT) carrier protein and from 2 to 200 μg, preferably 4 to 50 μg of diphtheria toxoid (DT) carrier protein. In a particular embodiment of the present invention, said vaccine contains from 18 to 32 μg of protein D carrier protein, from 10 to 20 μg tetanus toxoid (TT) carrier protein and from 6 to 12 μg diphtheria toxoid (DT) carrier protein.

In an embodiment, the vaccine of the invention comprises saccharide from serotypes 1, 4, 5, 6B, 7F, 9V, 14, and 23F individually conjugated to protein D, saccharide from serotype 18C conjugated to tetanus toxoid (TT) and saccharide from serotype 19F conjugated to diphtheria toxoid (DT) wherein each *S. pneumoniae* capsular saccharide is at a dose of 3 μg except for 4, 18C and 19F which is at a dose of 9 μg. In a particular embodiment of the present invention, said vaccine contains from 15 to 1500 μg, preferably 21 to 300 μg of protein D carrier protein, from 6 to 600 μg, preferably 12 to 150 μg of tetanus toxoid (TT) carrier protein and from 3 to 300 μg, preferably 6 to 75 μg of diphtheria toxoid (DT) carrier protein. In a particular embodiment of the present invention, said vaccine contains from 27 to 48 μg of protein D carrier protein, from 15 to 30 μg tetanus toxoid (TT) carrier protein and from 9 to 18 μg diphtheria toxoid (DT) carrier protein.

In an embodiment, the vaccine of the invention comprises saccharide from serotypes 1, 4, 5, 6B, 7F, 9V, 14, and 23F individually conjugated to protein D, saccharide from serotype 18C conjugated to tetanus toxoid (TT) and saccharide from serotype 19F conjugated to diphtheria toxoid (DT) wherein each *S. pneumoniae* capsular saccharide is at a dose of 4 μg except for 4, 18C and 19F which is at a dose of 12 μg. In a particular embodiment of the present invention, said vaccine contains from 20 to 2000 μg, preferably 28 to 400 μg of protein D carrier protein, from 8 to 800 μg, preferably 16 to 200 μg of tetanus toxoid (TT) carrier protein and from 4 to 400 μg, preferably 8 to 100 μg of diphtheria toxoid (DT) carrier protein. In a particular embodiment of the present invention, said vaccine contains from 36 to 64 μg of protein D carrier protein, from 20 to 40 μg tetanus toxoid (TT) carrier protein and from 12 to 24 μg diphtheria toxoid (DT) carrier protein.

In a particular embodiment of the present invention, the vaccine disclosed herein contain sodium chloride buffer as excipients.

In an embodiment, the pneumococcal vaccine to be used herein is the 10-valent conjugated pneumococcal vaccine sold uder the commercial name Synflorix™.

Further Adjuvant(s)

In some embodiments, the pneumococcal vaccines as disclosed herein comprise at least one, two or three adjuvant in addition to the at least one TLR-9 agonist adjuvant disclosed herein. The term "adjuvant" refers to a compound or mixture that enhances the immune response to an antigen. Antigens may act primarily as a delivery system, primarily as an immune modulator or have strong features of both. Suitable adjuvants include those suitable for use in mammals, including humans.

Examples of known suitable delivery-system type adjuvants that can be used in humans include, but are not limited to, alum (e.g., aluminum phosphate, aluminum sulfate or aluminum hydroxide), calcium phosphate, liposomes, oil-in-water emulsions such as MF59 (4.3% w/v squalene, 0.5% w/v polysorbate 80 (Tween 80), 0.5% w/v sorbitan trioleate (Span 85)), water-in-oil emulsions such as Montanide, and poly(D, L-lactide-co-glycolide) (PLG) microparticles or nanoparticles.

Examples of known suitable immune modulatory type adjuvants that can be used in humans include, but are not limited to saponins extracts from the bark of the Aquilla tree (QS21, Quil A), TLR4 agonists such as MPL (Monophosphoryl Lipid A), 3DMPL (3-O-deacylated MPL) or GLA-AQ, LT/CT mutants, cytokines such as the various interleukins (e.g., IL-2, IL-12) or GM-CSF, and the like.

Examples of known suitable immune modulatory type adjuvants with both delivery and immune modulatory features that can be used in humans include, but are not limited to ISCOMS (see, e.g., Sjölander et al. (1998) J. Leukocyte Biol. 64:713; WO90/03184, WO96/11711, WO 00/48630, WO98/36772, WO00/41720, WO06/134423 and WO07/026190) or GLA-EM which is a combination of a TLR4 agonist and an oil-in-water emulsion.

For veterinary applications including but not limited to animal experimentation, one can use Complete Freund's Adjuvant (CFA), Freund's Incomplete Adjuvant (IFA), Emulsigen, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and R1131, which contains three components extracted from bacteria, monophosphoryl lipid A, trehalose dimycolate and cell wall skeleton (MPL+ TDM+CWS) in a 2% squalene/Tween 80 emulsion.

Further exemplary adjuvants to enhance effectiveness of the pneumococcal vaccines as disclosed herein include, but are not limited to: (1) oil-in-water emulsion formulations (with or without other specific immunostimulating agents such as muramyl peptides (see below) or bacterial cell wall components), such as for example (a) SAF, containing 10% Squalane, 0.4% Tween 80, 5% pluronic-blocked polymer L121, and thr-MDP either microfluidized into a submicron emulsion or vortexed to generate a larger particle size emulsion, and (b) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+ CWS (DETOX™); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia), may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) (see e.g., GB-2220221, EP-A-0689454), optionally in the substantial absence of alum when used with pneumococcal saccharides (see e.g. WO00/56358); (6) combinations of 3dMPL with, for example, QS21 and/or oil-in-water emulsions (see e.g. EP-A-0835318, EP-A-0735898, EP-A-0761231); (7) a polyoxyethylene ether or a polyoxyethylene ester (see e.g. WO99/52549); (8) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (9) a saponin and an immunostimulatory oligonucleotide (e.g. a CpG oligonucleotide) (WO00/62800); (10) an immunostimulant and a particle of metal salt (see e.g. WO00/23105); (11) a saponin and an oil-in-water emulsion e.g. WO99/11241; (12) a saponin (e.g. QS21)+3dMPL+IM2 (optionally+a sterol) e.g. WO98/57659; (13) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

In a preferred embodiment, the pneumococcal vaccines as disclosed herein comprise alum, aluminium hydroxide, aluminum phosphate, or aluminum sulphate as additional adjuvant to the at least one TLR-9 agonist adjuvant disclosed herein.

In a particular embodiment of the present invention, the vaccine contains saccharide from serotypes 4, 6B, 9V, 14, 18C, 19F and 23F individually conjugated to CRM197 wherein each S. pneumoniae capsular saccharide is at a dose of 2 µg except for 6B which is at a dose of 4 µg, further comprising 0.5 mg aluminum phosphate, and optionally sodium chloride and sodium succinate buffer as excipients.

In a particular embodiment of the present invention, the vaccine contains saccharide from serotypes 4, 6B, 9V, 14, 18C, 19F and 23F individually conjugated to CRM197 wherein each S. pneumoniae capsular saccharide is at a dose of 4 µg except for 6B which is at a dose of 8 µg, further comprising 1 mg aluminum phosphate, and optionally sodium chloride and sodium succinate buffer as excipients.

In a particular embodiment of the present invention, the vaccine contains saccharide from serotypes 4, 6B, 9V, 14, 18C, 19F and 23F individually conjugated to CRM197 wherein each S. pneumoniae capsular saccharide is at a dose of 6 µg except for 6B which is at a dose of 12 µg, further comprising 1.5 mg aluminum phosphate, and optionally sodium chloride and sodium succinate buffer as excipients.

In a particular embodiment of the present invention, the vaccine contains saccharide from serotypes 4, 6B, 9V, 14, 18C, 19F and 23F individually conjugated to CRM197 wherein each S. pneumoniae capsular saccharide is at a dose of 8 µg except for 6B which is at a dose of 16 µg, further comprising 2 mg aluminum phosphate, and optionally sodium chloride and sodium succinate buffer as excipients.

In a particular embodiment of the present invention, the vaccine contains saccharide from serotypes 1, 3, 4, 5, 6A, 6B, 7F, 9V, 14, 18C, 19A, 19F, and 23F individually conjugated to CRM197 wherein each S. pneumoniae capsular saccharide is at a dose of 2 µg except for 6B which is at a dose of 4 µg further comprising 0.5 mg aluminum phosphate, and optionally sodium chloride and sodium succinate buffer as excipients.

In a particular embodiment of the present invention, the vaccine contains saccharide from serotypes 1, 3, 4, 5, 6A, 6B, 7F, 9V, 14, 18C, 19A, 19F, and 23F individually conjugated to CRM197 wherein each S. pneumoniae capsular saccharide is at a dose of 4 µg except for 6B which is at a dose of 8 µg further comprising 1 mg aluminum phosphate, and optionally sodium chloride and sodium succinate buffer as excipients.

In a particular embodiment of the present invention, the vaccine contains saccharide from serotypes 1, 3, 4, 5, 6A, 6B, 7F, 9V, 14, 18C, 19A, 19F, and 23F individually conjugated to CRM197 wherein each S. pneumoniae capsular saccharide is at a dose of 6 µg except for 6B which is at a dose of 12 µg further comprising 1.5 mg aluminum phosphate, and optionally sodium chloride and sodium succinate buffer as excipients.

In a particular embodiment of the present invention, the vaccine contains saccharide from serotypes 1, 3, 4, 5, 6A, 6B, 7F, 9V, 14, 18C, 19A, 19F, and 23F individually conjugated to CRM197 wherein each S. pneumoniae capsular saccharide is at a dose of 8 µg except for 6B which is at a dose of 16 µg further comprising 1.5 mg aluminum phosphate, and optionally sodium chloride and sodium succinate buffer as excipients.

In an embodiment, the pneumococcal vaccine is the 7-valent conjugated pneumococcal vaccine (Prevenar) or the 13-valent conjugated pneumococcal vaccine as disclosed in US2007/0184072 (13vPnC).

Immunocompromised Subjects

In a preferred embodiment of the present invention, the subject to be vaccinated with the vaccines of the present invention is an immunocompromised subject. Preferably said immunocomprimised subject is a mammal, such as a cat, sheep, pig, horse, bovine, dog or a human. In a most preferred embodiment, said subject is a human.

An immunocompromised individual is generally defined as a person who exhibits an attenuated or reduced ability to mount a normal humoral or cellular defense to challenge by infectious agents.

In an embodiment of the present invention, the immunocompromised subject to be vaccinated with the pneumococcal vaccine suffers from a disease or condition that impairs the immune system and results in an antibody response that is insufficient to protect against or treat pneumococcal disease.

In an embodiment, said disease is a primary immunodeficiency disorder. Preferably, said primary immunodeficiency disorder is selected from the group consisting of: combined T- and B-cell immunodeficiencies, antibody deficiencies, well-defined syndromes, immune dysregulation diseases, phagocyte disorders, innate immunity deficiencies, autoinflammatory disorders, and complement deficiencies.

In an embodiment, said combined T- and B-cell immunodeficiency is selected from the group consisting of: γc deficiency, JAK3 deficiency, interleukin 7 receptor chain α deficiency, CD45 deficiency or CD3δ/CD3ε deficiency, RAG 1/2 deficiency, DCLRE1C deficiency, adenosine deaminase (ADA) deficiency, reticular dysgenesis, Omenn syndrome, DNA ligase type IV deficiency, CD40 ligand deficiency, CD40 deficiency, Purine nucleoside phosphorylase (PNP) deficiency, MHC class II deficiency, CD3γ deficiency, CD8 deficiency, ZAP-70 deficiency, TAP-1/2 deficiency and Winged helix deficiency.

In an embodiment, said antibody deficiencies is selected from the group consisting of: X-linked agammaglobulinemia, btk deficiency, Bruton's agammaglobulinemia, µ-Heavy chain deficiency, I 5 deficiency, Igα deficiency, BLNK deficiency, thymoma with immunodeficiency, common variable immunodeficiency (CVID), ICOS deficiency, CD19 deficiency, TACI (TNFRSF13B) deficiency, BAFF receptor deficiency, AID deficiency, UNG deficiency, heavy chain deletions, kappa chain deficiency, isolated IgG subclass deficiency, IgA with IgG subclass deficiency, selective immunoglobulin A deficiency, specific antibody deficiency to specific antigens with normal B cell and normal Ig concentrations, transient hypogammaglobulinemia of infancy (THI).

In an embodiment, said well-defined syndrome is selected from the group consisting of: Wiskott-Aldrich syndrome, ataxia telangiectasia, ataxia-like syndrome, Nijmegen breakage syndrome, Bloom syndrome, DiGeorge syndrome (when associated with thymic defects), cartilage-hair hypoplasia, Schimke syndrome, Hermansky-Pudlak syndrome type 2, Hyper-IgE syndrome, Chronic mucocutaneous candidiasis, In an embodiment, said immune dysregulation disease is selected from the group consisting of: Chediak-Higashi syndrome, Griscelli syndrome type 2, perforin deficiency, MUNC13D deficiency, syntaxin 11 deficiency, X-linked lymphoproliferative syndrome, autoimmune lymphoproliferative syndrome: such as type 1a (CD95 defects), type 1b (Fas ligand defects), type 2a (CASP10 defects), type 2b (CASP8 defects), APECED (autoimmune polyendocrinopathy with candidiasis and ectodermal dystrophy) and IPEX (immunodysregulation polyendocrinopathy enteropathy X-linked syndrome)

In an embodiment, said phagocyte disorder is selected from the group consisting of: ELA2 deficiency (with myelodysplasia), GFI1 deficiency (with T/B lymphopenia), G-CSFR deficiency (G-CSF-unresponsive), Kostmann syndrome, Cyclic neutropenia, X-linked neutropenia/myelodysplasia, Leukocyte adhesion deficiency types 1, 2 and 3, RAC2 deficiency, Beta-actin deficiency, Localized juvenile periodontitis, Papillon-Lefèvre syndrome, Specific granule deficiency, Shwachman-Diamond syndrome, Chronic granulomatous disease: X-linked and autosomal forms, Neutrophil glucose-6-phosphate dehydrogenase deficiency, IL-12 and IL-23 β1 chain deficiency, IL-12p40 deficiency, Interferon γ receptor 1 deficiency, Interferon γ receptor 2 deficiency and STAT1 deficiency (2 forms).

In an embodiment, said innate immunity deficiency is selected from the group consisting of: Hypohidrotic ectodermal dysplasia, NEMO deficiency, IKBA deficiency, IRAK-4 deficiency, WHIM syndrome (warts, hypogammaglobulinaemia, infections, myleokathexis) and Epidermodysplasia verruciformis.

In an embodiment, said autoinflammatory disorder is selected from the group consisting of: Familial Mediterranean fever, TNF receptor associated periodic syndrome (TRAPS), Hyper-IgD syndrome (HIDS), CIAS1-related diseases, Muckle-Wells syndrome, Familial cold autoinflammatory syndrome, Neonatal onset multisystem inflammatory disease, PAPA syndrome (pyogenic sterile arthritis, pyoderma gangrenosum, acne) and Blau syndrome.

In an embodiment, said complement deficiency is selected from the group consisting of: C1q deficiency (lupus-like syndrome, rheumatoid disease, infections), C1r deficiency (idem), C4 deficiency (idem), C2 deficiency (lupus-like syndrome, vasculitis, polymyositis, pyogenic infections), C3 deficiency (recurrent pyogenic infections), C5 deficiency (Neisserial infections, SLE), C6 deficiency (idem), C7 deficiency (idem, vasculitis), C8a and C8b deficiency (idem), C9 deficiency (Neisserial infections), C1-inhibitor deficiency (hereditary angioedema), Factor I deficiency (pyogenic infections), Factor H deficiency (haemolytic-uraemic syndrome, membranoproliferative glomerulonephritis), Factor D deficiency (Neisserial infections), Properdin deficiency (Neisserial infections), MBP deficiency (pyogenic infections) and MASP2 deficiency. In an embodiment, said autoinflammatory disorder is selected from the group consisting of: C1, C2, C3, and C4 deficiencies.

In an embodiment of the present invention, the immunocompromised subject to be vaccinated suffers from a disease that affects the immune system wherein said disease is an acquired immunodeficiency disorder. Acquired immunodeficiency can be caused by several factors including bacterial or viral infections (such as HIV), cancers (such as leukaemia or myeloma), other chronic disorder but also aging, malnutrition, or various (such as glucocorticoids, chemotherapydrug treatments In a particular embodiment of the present invention, the immunocompromised subject to be vaccinated suffers from a disease selected from the groups consisting of: HIV-infection, acquired immunodeficiency syndrome (AIDS), cancer, chronic heart or lung disorders, congestive heart failure, diabetes mellitus, chronic liver disease, alcoholism, cirrhosis, spinal fluid leaks, cardiomyopathy, chronic bronchitis, emphysema, Chronic obstructive pulmonary disease (COPD), spleen dysfunction (such as sickle cell disease), lack of spleen function (asplenia), blood malignancy, leukemia, multiple myeloma, Hodgkin's disease, lymphoma, kidney failure, nephrotic syndrome and asthma.

In a particular embodiment, the immunocompromised subject to be vaccinated suffers from a disease selected from the groups consisting of: spleen dysfunction (such as sickle cell disease), lack of spleen function (asplenia), leukemia, multiple myeloma, Hodgkin's disease and lymphoma.

In a preferred embodiment, the immunocompromised subject to be vaccinated suffers from HIV-infection or acquired immunodeficiency syndrome (AIDS).

In a particular embodiment, the immunocompromised subject to be vaccinated suffers from HIV-infection or acquired immunodeficiency syndrome (AIDS), and is under therapy, said therapy consisting of taking at least one antiretroviral drug selected from the group consisting of a non-nucleosied reverse transcriptase inhibitor, a protease inhibitor and a nucleoside analog reverse transcriptase inihibitor (e.g. abacavir). In a particular embodiment, said therapy consists of taking at least three drugs belonging to at least two classes of antiretroviral drugs selected from the group consisting of non-nucleoside reverse transcriptase inhibitor, protease inhibitor and nucleoside analog reverse transcriptase inihibitor (e.g. abacavir). In a particular embodiment, said therapy consists of taking at least two nucleoside analogue reverse transcriptase inhibitors plus either a protease inhibitor or a non-nucleoside reverse transcriptase inhibitor.

In a particular embodiment, the immunocompromised subject to be vaccinated suffers from HIV-infection or acquired immunodeficiency syndrome (AIDS) and is under highly active antiretroviral therapy (HAART). In an embodiment said HAART consists of a 3 drug regimen which includes a non-nucleoside reverse transcriptase inhibitor, a protease inhibitor and/or a nucleoside analog reverse transcriptase inihibitor (e.g. abacavir) or a 2 drug regimen which includes a combination of a non-nucleoside reverse transcriptase inhibitor and a protease inhibitor.

In a particular embodiment, the immunocompromised subject to be vaccinated suffers from HIV-infection or acquired immunodeficiency syndrome (AIDS) and is not under highly active antiretroviral therapy (HAART), or is not under antiretroviral therapy, or said subject has never been exposed to antiretroviral drugs.

In a particular embodiment, the immunocompromised subject to be vaccinated is a non-viremic HIV infected patient. In another embodiment, the immunocompromised subject to be vaccinated is a viremic HIV infected patient.

In a particular embodiment of the present invention, the immunocompromised subject to be vaccinated suffers from tuberculosis or sexually transmitted diseases, e. g., syphilis or hepatitis.

In an embodiment of the present invention, the immunocompromised subject to be vaccinated suffers from malnutrition.

In an embodiment of the present invention, the immunocompromised subject to be vaccinated suffers from aging. In a particular embodiment of the present invention, the immunocompromised subject to be vaccinated is a human adult 55 years of age or older, more preferably a human adult 65 years of age or older. In an embodiment, the immunocompromised subject to be vaccinated is a human adult 70 years of age or older, 75 years of age or older or 80 years of age or older.

In a particular embodiment of the present invention, the immunocompromised subject to be vaccinated is taking a drug or treatment that lowers the body's resistance to infection.

In a particular embodiment of the present invention, the immunocompromised subject to be vaccinated is taking a drug selected from the group consisting of chemotherapy (e.g. cancer drugs), disease-modifying antirheumatic drugs, immunosuppressive drugs after organ transplants and glucocorticoids.

In an embodiment of the present invention, the immunocompromised subject to be vaccinated is taking an oral immunosuppressant drug selected from the group consisting of: tacrolimus (Prograf), mycophenolate mofetil (CellCept), sirolimus (Rapamune), prednisone, cyclosoporine (Neoral, Sandimmune, Gengraf) and azathioprine (Imuran). In an embodiment, the immunocompromised subject is taking at least two or three of said oral immunosuppressant drugs.

In an embodiment of the present invention, the immunocompromised subject to be vaccinated is taking an immunosuppressant drug selected from the group consisting of: Everolimus, Mycophenolic acid, Corticosteroids (such as Prednisolone or Hydrocortisone), Monoclonal anti-IL-2Rα receptor antibodies (such as Basiliximab or Daclizumab), Anti-thymocyte globulin (ATG) and Anti-lymphocyte globulin (ALG). In an embodiment, the immunocompromised subject is taking at least two or three of said immunosuppressant drugs.

In a particular embodiment of the present invention, the immunocompromised subject to be vaccinated has undergone organ transplant, or bone marrow transplant or cochlear implantation.

In a particular embodiment of the present invention, the immunocompromised subject to be vaccinated has undergone radiation therapy.

In a particular embodiment of the present invention, the immunocompromised subject to be vaccinated is a smoker.

In a particular embodiment of the present invention, the immunocompromised subject to be vaccinated suffers from asthma and is treated with oral corticosteroid therapy.

In a particular embodiment of the present invention, the immunocompromised subject to be vaccinated is an Alaskan native or an American Indian.

In a particular embodiment of the present invention, the immunocompromised subject to be vaccinated has a white blood cell count (leukocyte count) below $5 \times 10^9$ cells per liter, or below $4 \times 10^9$ cells per liter, or below $3 \times 10^9$ cells per liter, or below $2 \times 10^9$ cells per liter, or below $1 \times 10^9$ cells per liter, or below $0.5 \times 10^9$ cells per liter, or below $0.3 \times 10^9$ cells per liter, or below $0.1 \times 10^9$ cells per liter. White blood cell count (leukocyte count): The number of white blood cells (WBCs) in the blood. The WBC is usually measured as part of the CBC (complete blood count). White blood cells are the infection-fighting cells in the blood and are distinct from the red (oxygen-carrying) blood cells known as erythrocytes. There are different types of white blood cells, including neutrophils (polymorphonuclear leukocytes; PMNs), band cells (slightly immature neutrophils), T-type lymphocytes (T cells), B-type lymphocytes (B cells), monocytes, eosinophils, and basophils. All the types of white blood cells are reflected in the white blood cell count. The normal range for the white blood cell count is usually between 4,300 and 10,800 cells per cubic millimeter of blood. This can also be referred to as the leukocyte count and can be expressed in international units as $4.3\text{-}10.8 \times 10^9$ cells per liter.

In a particular embodiment of the present invention, the immunocompromised subject to be vaccinated suffers from neutropenia. In a particular embodiment of the present invention, the immunocompromised subject to be vaccinated has a neutrophil count below $2 \times 10^9$ cells per liter, or below $1 \times 10^9$ cells per liter, or below $0.5 \times 10^9$ cells per liter, or below $0.1 \times 10^9$ cells per liter, or below $0.05 \times 10^9$ cells per liter. A low white blood cell count or "neutropenia" is a condition characterized by abnormally low levels of neutrophils in the circulating blood. Neutrophils are a specific kind of white blood cell that help prevent and fight infections. The most common reason that cancer patients experience neutropenia is as a side effect of chemotherapy. Chemotherapy-induced neutropenia increases a patient's risk of infection and disrupts cancer treatment.

The fewer the neutrophils in the blood and the longer patients remain without enough neutrophils, the more susceptible patients are to developing a bacterial or fungal infection. Neutrophils are a major component of antibacterial defense mechanisms. As the neutrophil count falls below 1.0, 0.5, and $0.1 \times 10^9/L$, the frequency of life-threatening infection rises steeply from 10% to 19% and 28%, respectively.

In a particular embodiment of the present invention, the immunocompromised subject to be vaccinated has a CD4+ cell count below 500/mm3, or CD4+ cell count below 300/mm3, or CD4+ cell count below 200/mm3, CD4+ cell count below 100/mm3, CD4+ cell count below 75/mm3, or CD4+ cell count below 50/mm3.

CD4 cell tests are normally reported as the number of cells in mm3. Normal CD4 counts are between 500 and 1600, and CD8 counts are between 375 and 1100. CD4 counts drop dramatically in people with HIV.

In an embodiment of the invention, any of the immunocompromised subject disclosed herein is a human male or a human female.

Regimen

In some cases, as little as one dose of the vaccine according to the invention is needed, but under some circumstances, such as conditions of greater immune deficiency, a second, third or fourth dose may be given.

In an embodiment, a prime dose is given at day 0 and one or more boosts are given at intervals that range from about 2 to about 24 weeks, preferably with a dosing interval of 4-8 weeks.

In an embodiment, a prime dose is given at day 0 and a boost is given about 3 months later.

As shown in the example part, some of the shortcomings of current vaccination can be overcome using the vaccine of the invention. In particular the vaccine of the invention may reduce the number of vaccinations required to achieve seroprotection, accelerate seroconversion, possibly permitting post-exposure vaccination, reduce the proportion of non-responders, reduce the amount of antigen required, increase antibody avidity and protective activity and/or lead to a more sustained antibody levels. These advantages are particularly interesting when treating immunocompromised patients.

EXAMPLE

Example 1

Immune Response to Toll-Like Receptor 9-agonist Adjuvated Pneumococcal Vaccination in HIV-Infected Adults A phase II study of 96 HIV infected patients has been undertaken.
Objectives:
 Primary Objective:
  To compare numbers of vaccine highresponders—defined as 2-fold increase and IgG levels≥1 µg/mL to at least 5 of 7 pneumococcal serotypes (by quantitative IgG measurements)—in the CpG 7909 group vs. the control group.
 Secondary Objectives:
  To compare the qualititative (functional) antibody response to pneumococcal vaccination with or without CpG 7909
  To evaluate safety and tolerance of CpG 7909 as a pneumococcal vaccine adjuvant
  To analyse changes in pneumococcal carrier status after pneumococcal vaccination
Main Assessment Parameters:
 Efficacy:
  Primary: Quantitative measurement of specific anticapsular antibodies (7 serotypes)
  Secondary: Functional activity of specific anticapsular antibodies (pneumococcal serotypes 6B, 14, 19F and 23F); Number and intensity of adverse and serious adverse events; Microbiological changes in pneumococcal pharangyal colonization; Baseline CD4-count and measurement of sCD163
 Safety/Tolerability:
  Adverse events (AEs); Serious adverse events (SAEs); Laboratory tests (hematology, clinical chemistry i.e. viral load (HIV RNA) and CD4-count); Physical examination.
STUDY DESIGN: Placebo-controlled, randomized, double-blinded study. TOTAL SAMPLE SIZE: 96 participants (48 per group).
TEST DRUGS AND FORMULATIONS: CpG 7909 (a synthetic Toll-like receptor 9-agonist) formulated in PBS buffer. CPG 7909 is a B-Class CpG ODN of sequence 5'-TCGTCGTTTTGTCGTTTTGTCGTT-3' (SEQ ID NO: 5) and has been synthesized with a wholly phosphorothioate backbone.
TEST DRUG DOSAGE: 1 mg CpG 7909 (100 µl) mixed with each pneumococcal vaccination.
CONTROLS: 100 µl of a neutral PBS buffer (identical in colour and viscosity to the test drug) with each pneumococcal vaccine.
ROUTE OF ADMINISTRATION: Intramuscular injection. BLINDING: Double-blinded study.
ENROLMENT: Randomization;
 Eligible patients have been randomized in a ratio of 1:1 to receive pneumococcal vaccination with or without CpG 7909.
Immunization:
 Vaccines were kept in their original container according to manufacturer's description and mixed with the adjuvant (CpG 7909 or Placebo) immediately before immunization. Immunization has been done in the left or right upper deltoid muscle at the preference of the subject.

DURATION OF TRIAL FOR EACH PARTICIPANT: 10 months from 1st vaccination to last follow-up.

Subject Withdrawal from the Study:

From an analysis perspective, a "withdrawal" from the study is any subject who did not come back for the concluding visit foreseen in the protocol.

A subject qualifies for "withdrawal" from the study when no study procedure has occurred, no follow-up has been performed and no further information has been collected for this subject from the date of withdrawal/last contact.

Withdrawals has not been replaced.

Subject Withdrawal from Investigational Product

A withdrawal from the investigational product is any subject who does not receive the complete treatment, i.e. when no further planned dose is administered from the date of withdrawal. A subject withdrawal from the investigational product may not necessarily be withdrawn from the study as further study procedures or follow-up may be performed (safety or immunogenicity) if planned in the protocol.

Data to be Included in the Case Report Form:
  Birthday, sex, race, height, weight, study number
  Adverse events reported by subject including starting point and duration (time to resolution)
  Positive findings during physical examination
  Medical history
  Other vaccinations received outside the study during the study period
  Any changes in regular medication during the time of study
  Pre-existing conditions or signs and/or symptoms present in a subject prior to the start of the study/first vaccination
  All laboratory findings during the time of the study Participant Inclusion Criteria:
  1) Written informed consent and authority statement provided according to local regulatory and ethical practice using a participant information sheet and informed consent form approved by the responsible Ethics Committee.
  2) Male or female participants aged>=18 years.
  3) HIV-seropositive individuals Participant Exclusion Criteria:
  1) Pregnancy as determined by a positive urine beta-hCG (if female).
  2) Participant unwilling to use reliable contraception methods for the duration of the trial. Reliable methods of birth control include: pharmacologic contraceptives including oral, parenteral, and transcutaneous delivery; condoms with spermicide; diaphragm with spermicide; surgical sterilization; vaginal ring; intrauterine device; abstinence; and postmenopause (if female).
  3) Currently breast-feeding (if female).
  4) Latest CD4 count<200×10$^6$ cells/µL
  5) Viral load (HIV RNA)>50 copies/mL if on HAART (defined as at least three antiretrovirals including either a protease inhibitor or a NNRTI, i.e. combivir 300/150 mg×2+ stocrin 600 mg×1 for a minimum of 6 months)
  6) Previous enrollment in this study.
  7) Any medical, psychiatric, social, or occupational condition or other responsibility that, in the judgment of the Principal Investigator (PI), would interfere with the evaluation of study objectives (such as severe alcohol abuse, severe drug abuse, dementia).
  8) Unable to follow protocol regimen
  9) Pneumococcal vaccination 5 years or less prior to inclusion
  10) Planned participation in other vaccination trials during the time of the study Procedures:

Consenting participants that pass the inclusion/exclusion criteria have been enrolled in the study. Blood samples for baseline parameter measurements have been drawn before proceeding to immunization. At randomization, participants has been allocated 1:1 one of two study regimens:

Experimental group: Two doses of 7-valent conjugate pneumococcal vaccination (Prevenar®, Wyeth)+1 mg CpG 7909 (day 0), two doses of 7-valent conjugate pneumococcal vaccination (Prevenar®, Wyeth)+1 mg CpG 7909 (day 90) and one dose of 23-valent polysaccharide vaccine (Pneumo Novum®, Sanofi Pasteur MSD)+1 mg CpG 7909 (day 270)

Control group: Two doses of 7-valent conjugate pneumococcal vaccination (Prevenar®, Wyeth)+100 µl of placebo (day 0), two doses of 7-valent conjugate pneumococcal vaccination (Prevenar®, Wyeth)+100 µl of placebo (day 90) and one dose of 23-valent polysaccharide vaccine (Pneumo Novum®, Sanofi Pasteur MSD)+100 µl of placebo (day 270).

Blood samples were drawn and follow-up by the physician included physical examination and medical history, registration of AEs (Adverse Event)/SAEs (Serious Adverse Event), vaccination history outside the study and any other information that may be relevant to document in the CRF. A concluding visit was conducted at day 300.

A subject who returned for the concluding visit or was available for the concluding contact foreseen in this protocol was considered to have completed the study.

Vaccines and Test Drug/Placebo Injections:

All subjects were dosed at 0, 90 and 270 days. All immunizations were done in the deltoid muscle of the right or left arm (according to the participants preference).

At day 0 and 90 study participants received one intramuscular injections of double dose Prevenar 1.0 ml+0.1 ml test drug (CpG 7909)/placebo. In both cases, the volume injected into the arm is 1.1 ml.

At day 270 study participants receives one intramuscular injections of 0.5 ml Pneumo Novum+0.1 ml test drug (CpG 7909)/placebo. In all cases, the volume injected into the arm is 1.1 ml.

Investigators and participants were not aware of whether experimental or control injection was administered. The volume and appearance of each injection product were identical.

Primary Efficacy Parameter and Analysis of Antibody Response

The study was powered to detect differences between the experimental group and the control group in Pneumococcal vaccine high responders defined as 2-fold increase and IgG levels µg/mL to at least 5 of 7 pneumococcal serotypes (by quantitative IgG measurements). The study was not powered to detect differences in the incidence of pneumonia or confirmed pneumococcal disease invasive/non-invasive. This would require a substantial number of participants and a longer follow-up period. The most widely used measurement of immune response to pneumococcal vaccination is quantitative detection of serotype specific anticapsular antibodies. Recent data indicate that the specificity of this method can be improved by incorporation a 22F absorption step; thereby removing crossreacting antibodies of low avidity. Quantitative serotype specific IgG measurements were done by Statens Serum Institut (SSI), Copenhagen, Denmark using an ELISA incorporating the 22F absorption step. SSI were blinded in regards to treatment allocation.

Secondary Efficacy Parameter and Analysis of Antibody Response

Measuring the quantitative amount of serotype specific anticapsular antibodies does not give any information the functionality of the antibodies. This can be measured by a flow-cytometric opsonophagocytic assay and gives indirect information on the antibodies ability to opsonize and facilitate killing of invading pneumococci.

Qualitative analysis was done using a flowcytometric opsonophagocytic assay which measures functional (opsonophagocytic) activity (OPA) of the serotype specific antibodies. In short: Eight twofold dilutions are made in OPA buffer from 10 µl of test serum. A 20-µl aliquot of either multiplex bacteria or multiplex bead suspension containing $1\times10^5$ of each of the target pneumococcal serotype or pneumococcal polysaccharide-conjugated beads is added to each well, and the plate is incubated for one hour at 37° C. with horizontal shaking (200 rpm). Following this, 20 µl of sterile serum from 3- to 4-week-old baby rabbit serum (Pel-Freez, Brown Deer, Wis.) is added to each well except for HL60 cell control wells, which receives 20 µl of OPA buffer. After incubation at 37° C. for 20 min with shaking (200 rpm on an orbital shaker), 30 µl of washed HL60 polymorphonuclear leukocytes (PMNs) (2.5µ 104/ml) are added to each well, resulting in an effector-to-target ratio of 1:4 (for each target type). The final well volume is 80 µl, with the first well of a dilution series containing a 1:8 final dilution. The plate is then incubated for 60 min with shaking at 37° C. An additional 80 µl of OPA buffer is added to every well to provide sufficient volume for flow cytometric analysis and the well contents transferred to microtiter tubes (Bio-Rad, Hercules, Calif.). Up to 12 serum samples can be assayed per plate, including a quality control sample. Flow analysis were done by Flow Applications, Inc, Ill, USA51.

Pneumococcal Carriage

Pneumococcal vaccination can affect pharyngeal carriage of pneumococci. Pneumococcal pharyngeal colonization may also affect the immune response to pneumococcal vaccination. Therefore it is important to establish carrier status before and after pneumococcal vaccination. Oropharyngeal colonization has been tested in the posterior pharynx using a BBL culture swap (Becton Dickson Microbiology Systems, Cockeysville, Md., USA) thru the oral cavity. Samples were labelled with the individuals study ID number, frozen at −20° C. within few hours and later shipped to Statens Serum Institut, where isolation, culturing and serotyping took place. This has taken place at day 0 and again during follow-up at day 270.

Adverse Events (AEs):

An AE is any untoward medical occurrence in a clinical investigation subject, temporally associated with the use of a medicinal product, whether or not considered related to the medicinal product.

An AE can therefore be any unfavorable and unintended sign (including an abnormal laboratory finding), symptom or disease (new or exacerbated) temporally associated with the use of a medicinal product. In this study an AE has been graded according to the Common Toxicity Criteria, version 2.0.

Serious Adverse Event (SAE) Definition:

An adverse event occurring during a clinical trial is any undesirable experience associated with the use of a medical product in a participant. The event is serious and will be reported to the regulatory authority when the participant outcome is:
1. Death
2. Life-Threatening
3. Hospitalization (initial or prolonged)
4. Disability
5. Requiring Intervention to Prevent Permanent Impairment or Damage
6. Congenital disorder/anomaly (for pregnant women)

Suspected Unexpected Serious Adverse Event Reaction (SUSAR) Definition:

A Suspected Unexpected Serious Adverse Reaction (SUSAR) occurring during the study and is to be reported:
The event must be a SAE.
There must be a certain degree of probability that the event is an adverse reaction on the administered drug.
The adverse reaction must be unexpected, that is to say, not foreseen in the Investigator's Brochure (for an unauthorised medicinal product).

Data Evaluation: Criteria for Evaluation of Objectives

All endpoints has been compared between the experimental vaccine group (+CpG 7909) and the control vaccine group (+placebo).

A substudy compared endpoints in the two (non-randomised) treatment groups (on HAART vs. no HAART)

Primary Endpoints:
At six months after 2nd vaccination with Prevenar.
Pneumococcal vaccine high responders defined as 2-fold increase and IgG levels≥1 µg/mL to at least 5 of 7 pneumococcal serotypes (by quantitative IgG measurements)

Secondary Endpoints:
Immunogenicity
At three months after 1st vaccination with Prevenar.
Pneumococcal vaccine high responders defined as 2-fold increase and IgG levels≥1 µg/mL to at least 5 of 7 pneumococcal serotypes (by quantitative IgG measurements)
Opsonophagocytic activity for serotypes 6B, 14, 19F and 23F expressed as titers
Serotype-specific antibody response defined as 2-fold increase and IgG levels≥1 µg/mL
Serotype-specific antibody response defined as change in IgG levels
At six months after 2nd vaccination with Prevenar.
Opsonophagocytic activity for serotypes 6B, 14, 19F and 23F expressed as titers
Serotype-specific antibody response defined as 2-fold increase and IgG levels≥1 µg/mL
Serotype-specific antibody response defined as change in IgG levels
At one month after vaccination with Pneumo Novum.
Pneumococcal vaccine high responders defined as 2-fold increase and IgG levels≥1 µg/mL to at least 5 of 7 pneumococcal serotypes (by quantitative IgG measurements)
Opsonophagocytic activity for serotypes 6B, 14, 19F and 23F expressed as titers
Serotype-specific antibody response defined as 2-fold increase and IgG levels≥1 µg/mL
Serotype-specific antibody response defined as change in IgG levels
Geometric Mean Antibody Concentrations With the Standard Enzyme Immunoassay for serotypes 1, 4, 7F, 9V, 14, 18C and 19F
Pharyngeal Colonization
At six months after 2nd vaccination with Prevenar.
Number of individuals with pneumococcal colonization
Predictors of Antibody Response
At baseline.
Risk factors for vaccine response at six months after 2nd vaccination with Prevenar, Secondary Endpoints:
REACTOGENICITY AND SAFETY IN ALL SUBJECTS
Analysis Populations:
Safety population: all patients who received at least one vaccination.

Occurrence of solicited and general symptoms during the 4-day (day 0 to Day 3) period after each vaccination dose Occurrence of unsolicited symptoms up to 1 month after each vaccination Changes in CD4-count and viral load during the study Safety is assessed by physical examination, adverse events (according to common toxicity criteria version 2.0), laboratory tests, and HIV control parameters (HIV RNA and CD4-count).

Statistical Analyses
Baseline Characteristics

Differences between study groups at day 0 will be assessed by Mann-Whitney rank sum test (continuous variables) and Chi-square test (dichotomous and categorical variables).

Primary Endpoint

Prevalence ratios of high responders at six months after 2nd vaccination with Prevenar, comparing the two vaccination scheme groups (with/without CpG 7909), has been estimated by Chi-square test. A Poisson regression model adjusted by age, CD4 cell count at baseline and HAART (on HAART vs. no HAART) at baseline is planned.

Secondary Endpoints

Comparison of endpoints between the study groups has been done by Chi-square test. A Poisson regression (dichotomous endpoints) or linear regression (continuous endpoints), adjusted for appropriate potential confounders is planned.

Risk factors for achieving a high vaccination response (classified as a high responder) at six months after 2nd vaccination with Prevenar will be estimated by multivariate Poisson regression.

Safety Data

Safety data have been listed and compared by Chi-square test.

Estimated Sample Size

Intention-to-treat (ITT) population: all randomized participants

Sample size is calculated for the primary endpoint (prevalence ratios of high responders at six months after 2nd vaccination with Prevenar, comparing the two vaccination scheme groups). Setting the probabilities of Type I and Type II error to:

Type I error probability ($\alpha$)=0.05 (two-sided).

Type II error probability ($\beta$)=0.20 (power=1−$\beta$=0.80).

Primary endpoint: proportion of vaccine highresponders (defined as 2-fold increase and IgG levels≥1 µg/mL to at least 5 of 7 pneumococcal serotypes).

N is the number of participants needed in each group.

| Control\CpG | 0.50 | 0.55 | 0.60 | 0.65 | 0.70 |
|---|---|---|---|---|---|
| 0.20 | 39 | 29 | 23 | 18 | 15 |
| 0.25 | 58 | 41 | 31 | 24 | 19 |
| 0.30 | 93 | 61 | 42 | 31 | 24 |
| 0.35 | 170 | 96 | 62 | 43 | 31 |
| 0.40 | 388 | 173 | 97 | 62 | 42 |

Assuming a prevalence of 30% in control vaccine the group and a prevalence of 60% in the experimental vaccine group a sample size of 42 patients per group is required to detect a difference in prevalence estimated by Poisson regression. The expected drop-out percentage is set to 10%. Thus, a total of 94 subjects were needed in the study.

In accordance with the approach recommended by regulatory authorities, the two-sided 95% confidence interval (CI) of the immune response difference has been calculated.

Example 2

Immunogenicity and Safety of TLR9-Adjuvanted Pneumococcal Vaccines in HIV-Infected Adults. Results of the Randomized, Double-Blind, Placebo-Controlled Trial The clinical trial described in example 1 was conducted.

The study was a placebo-controlled phase II trial randomizing persons with HIV to be vaccinated with double doses of PCV (pneumococcal conjugate vaccine) (Prevnar) ±1 mg CpG 7909 at 0 and 3 months and with one single dose of PPV (pneumococcal polysaccharide vaccine) ±1 mg CpG 7909 at 9 months. Immunogenicity and safety were evaluated at 0, 3, 4, 9, and 10 months. Primary endpoint was proportion of vaccine high-responders defined as 2-fold increase and IgG levels≥1 µg/mL to at least 5 of 7 PCV serotypes (quantitative IgG by ELISA, Statens Serum Institute, Copenhagen, Denmark) at 9 months.

Results: As shown in table 1, 96 participants were included. In each group of 48 participants, 38 were on ART.

TABLE 1

Baseline characteristics at time of inclusion

| | | Placebo group | CPG group |
|---|---|---|---|
| n | | 48 | 48 |
| Sex | | | |
| | Male | 38 (79.2) | 43 (89.6) |
| | Female | 10 (20.8) | 5 (10.4) |
| Race | | | |
| | Caucasian | 43 (89.6) | 47 (97.9) |
| | Non-caucasian | 5 (10.4) | 1 (2.1) |
| Median age, years (IQR) | | 48.9 (42.0-59.0) | 48.9 (43.0-58.8) |
| Median CD4+ cell count per ml × $10^6$ (IQR) | | 617 (500-848) | 673 (393-817) |
| On HAART | | | |
| | Yes | 38 (79.2) | 38 (79.2) |
| | No | 10 (20.8) | 10 (20.8) |
| Median log HIV RNA, IQR | | | |
| | On HAART | 1.60 | 1.60 |
| | No HAART | 4.47 (3.73-4.86) | 4.25 (3.70-4.59) |
| Previous PPV-23 immunization* | | 1 (2.1) | 2 (4.2) |
| Current smoker | | 17 (35.4) | 18 (37.5) |

*>5 year prior to inclusion.
IQR: Interquartile range

As shown in table 3 and FIG. 1, the proportion of vaccine high-responders were significantly higher in the CpG than in the placebo adjuvant group (48.8% vs. 25.0%, p=0.018) following PCV immunization.

Increased responses were also observed at 3 (51.1% vs. 39.6%, p=0.26), 4 (77.3% vs. 56.3%, p=0.033), and 10 (87.8% vs. 51.1%, p<0.001) months.

TABLE 3

Proportion of vaccine high-responders at each time-point.

| n (%) | | Placebo group | CPG group | p |
|---|---|---|---|---|
| HR Pre PCV1 | yes | 0 | 0 | — |
| | no | 0 | 0 | |
| HR 3 months post PCV1 | yes | 19 (39.6) | 24 (51.1) | 0.26 |
| | no | 29 (60.4) | 23 (48.9) | |
| HR 1 month post PCV2 | yes | 27 (56.3) | 34 (77.3) | 0.03 |
| | no | 21 (43.7) | 10 (22.7) | |
| HR 6 months post PCV2 | yes | 12 (25.0) | 21 (48.8) | 0.02 |
| | no | 36 (75.0) | 22 (51.2) | |
| HR 1 month post PPV-23 | yes | 24 (51.1) | 36 (87.8) | <0.001 |
| | no | 23 (48.9) | 5 (12.2) | |

Figure 2:
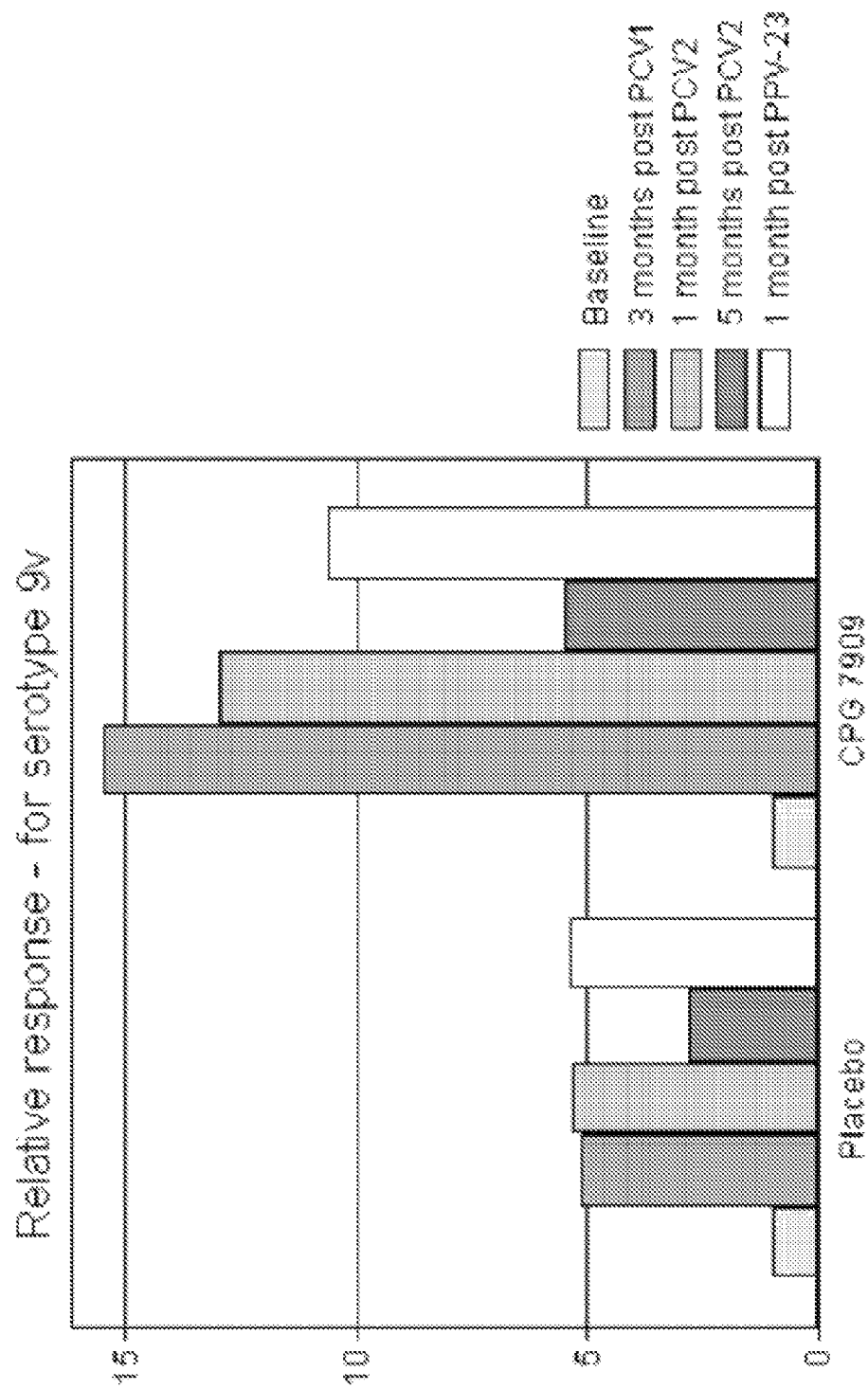
FIG. 2 shows the difference in relative IgG response for PCV serotype 9v between the CPG-7909 and placebo groups.
Figure 3:
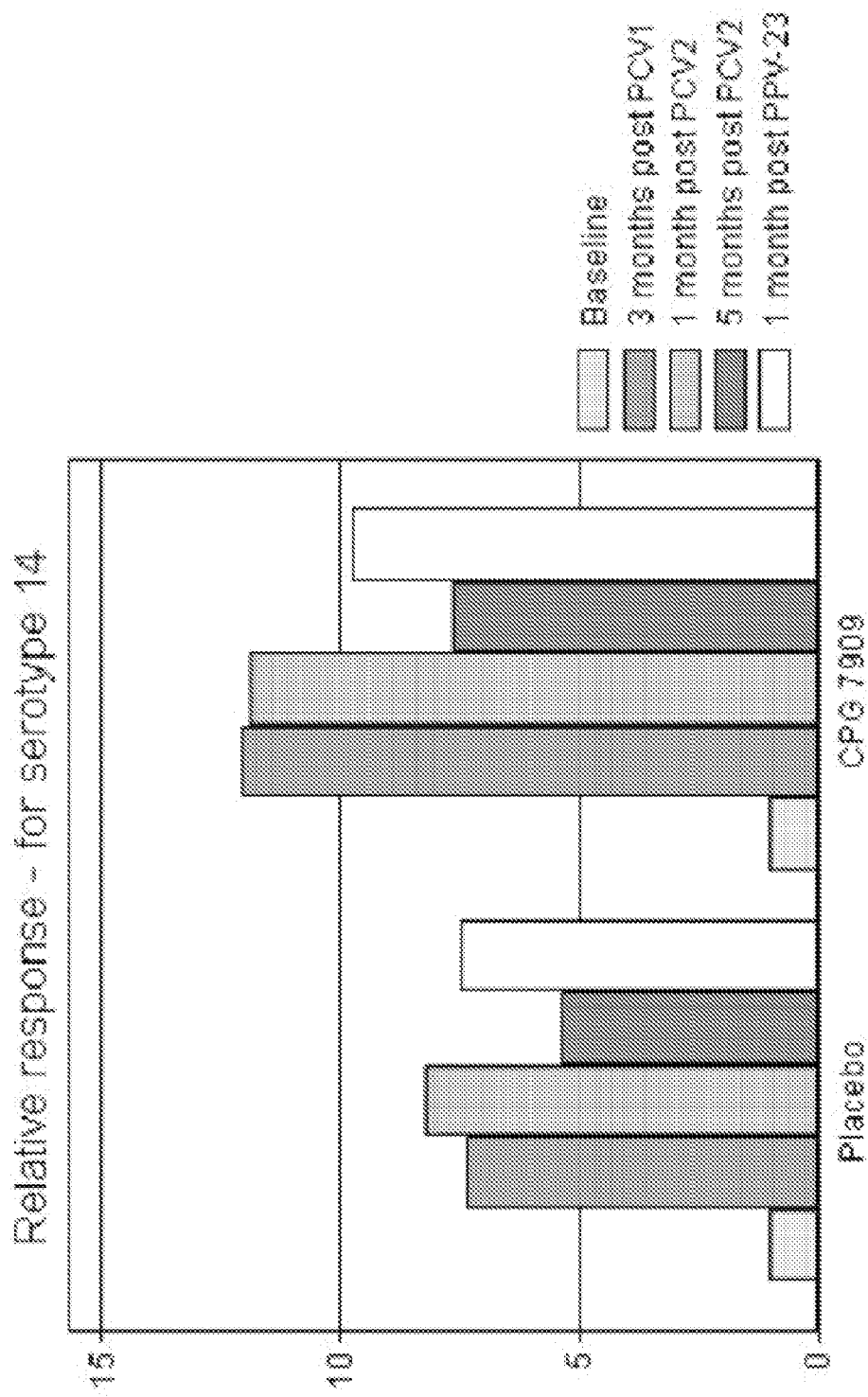
FIG. 3 shows the difference in relative IgG response for PCV serotype 14 between the CPG-7909 and placebo groups.

HR: pneumococcal vaccine highresponders - defined as 2-fold increase and IgG levels ≥ 1 µg/mL to at least 5 of the 7 Prevnar pneumococcal serotypes (by quantitative IgG measurements);
PCV: Pneumococcal conjugate vaccine;
PPV-23: 23-valent pneumococcal polysaccharide vaccine FIGS. 2 and 3 show the difference in relative IgG response for two PCV serotypes (9v and 14) between the CPG and placebo group.

Figure 4:
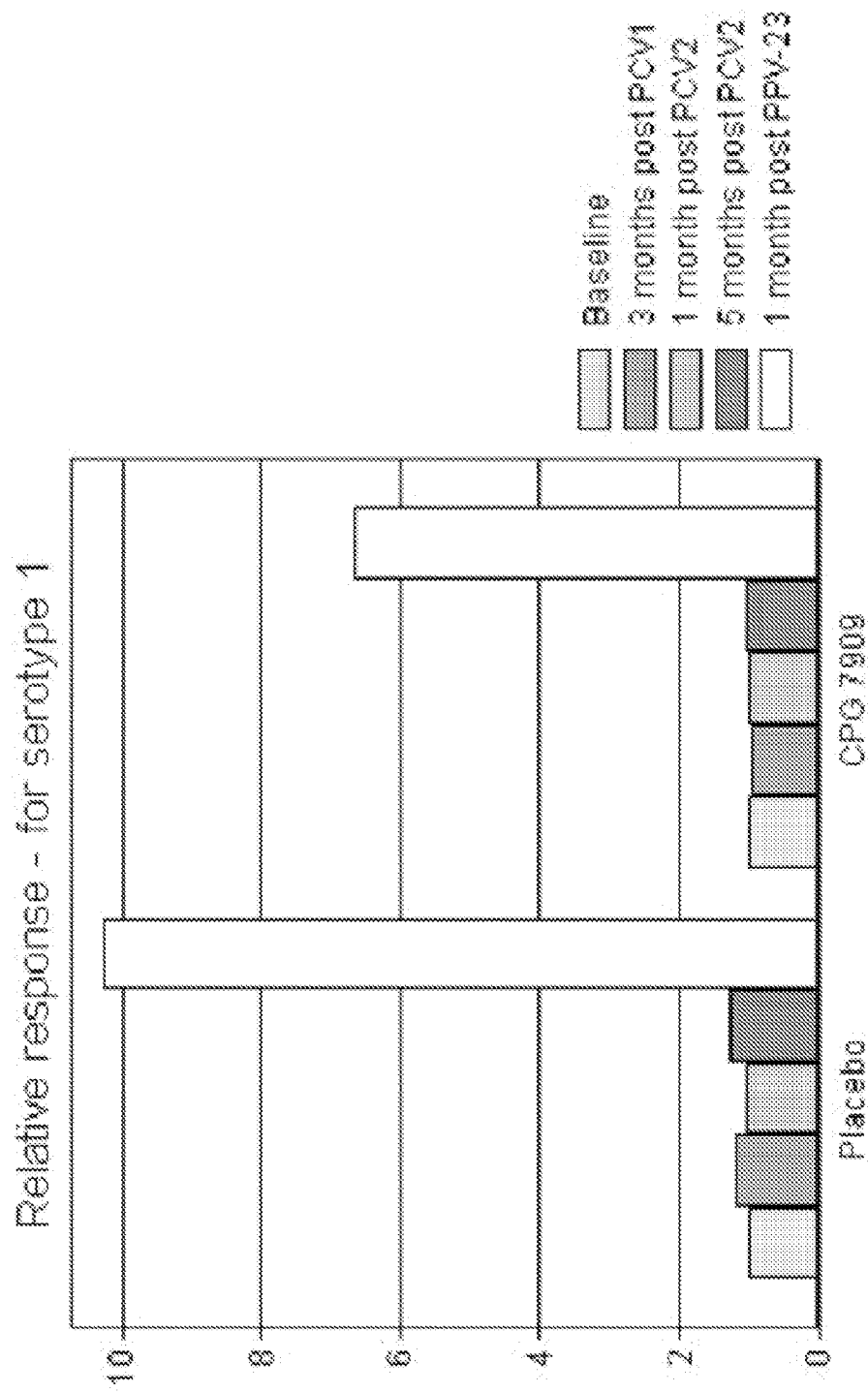
FIG. 4 shows the relative IgG response for non-PCV serotype 1 between the CPG-7909 and placebo groups.
Figure 5:
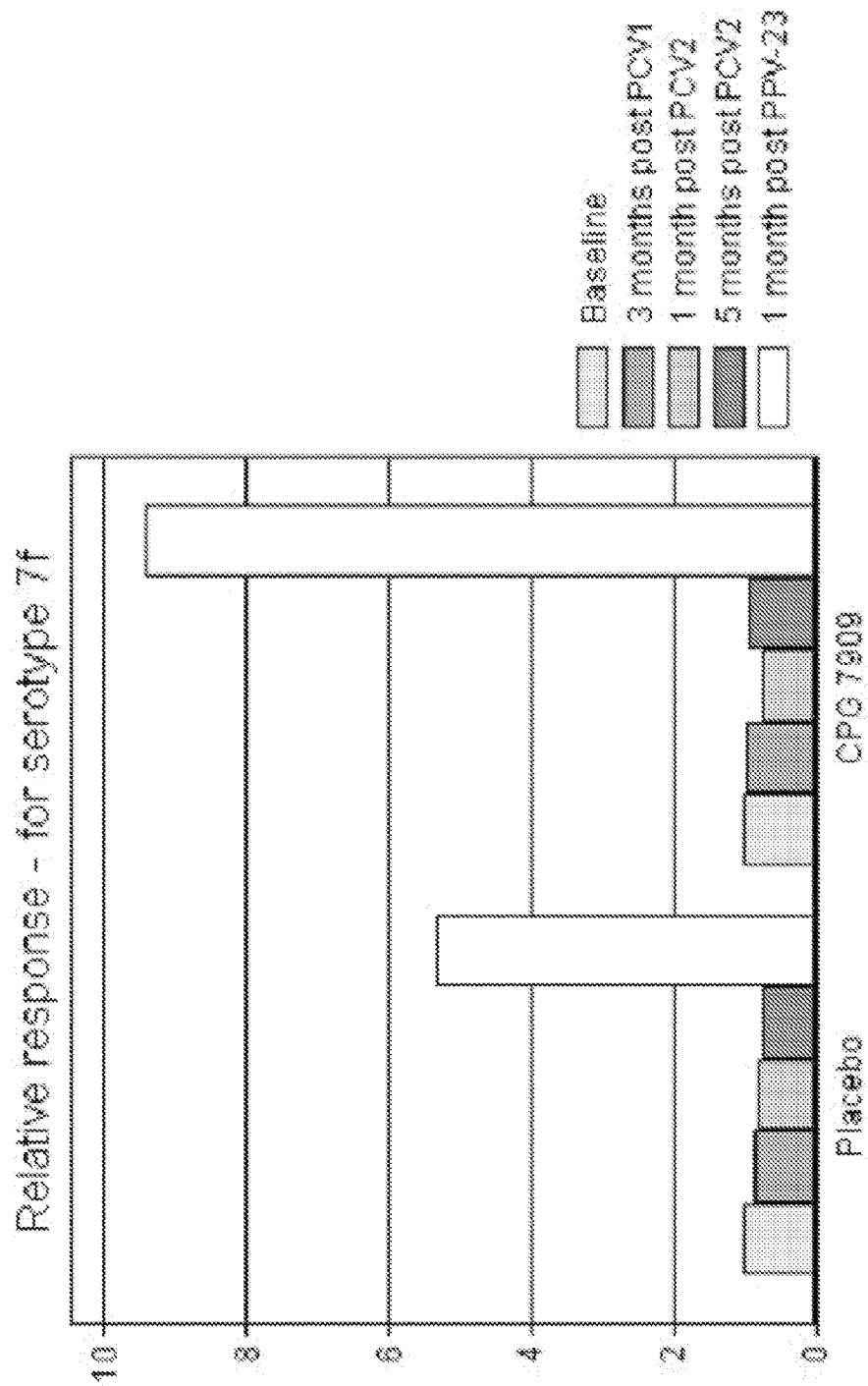
FIG. 5 shows the relative IgG response for non-PCV serotype 7f between the CPG-7909 and placebo groups.

FIGS. 4 and 5 show the relative IgG response for two non-PCV serotypes (1 and 7f) in the CPG and placebo group (as expected no increase in IgG was observed in relation to PCV immunization).

Following PPV immunization, both groups (+/−CpG) show significant responses. However, CpG did not increase the antibody response to non-PCV serotypes (1 and 7f) after PPV immunization.

As shown in table 4 (pages 37-38), data on geometric mean concentrations (GMC) of IgG antibodies revealed increasing GMC-ratios from baseline to months 3, 4, 9 and 10 for nearly all PCV-7-serotypes for the experimental group compared to the control group. As expected GMC of the 3 non-PCV serotypes (1, 7F and 19A) did not change significantly following PCV-7 immunization. Following PPV-23 both groups experienced a 2-5 fold increase in GMC for non-PCV-7 serotypes (lowest for serotype 19A) but there were no significant group-differences in GMC-ratios.

TABLE 4

Geometric mean concentrations of IgG antibodies and geometric mean of OPA titers of persons with HIV receiving pneumococcal vaccines with or without CPG 7909.

| PCV-7 serotypes | Group | Pre 1$^{st}$ PCV-7 | GM-ratio | Post 1$^{st}$ PCV-7 | GM-ratio | Post 2$^{nd}$ PCV-7 |
|---|---|---|---|---|---|---|
| PS 4 - IgG | CPG 7909 | 0.53 (0.26-0.81) | | 1.35 (0.95-1.90) | | 2.26 (1.65-3.10) |
| | Control | 0.39 (0.32-0.49) | 0.81 (0.58-1.13) | 1.26 (0.90-1.77) | 1.07 (0.66-1.73) | 1.48 (1.09-2.00) |
| PS 6B - IgG | CPG 7909 | 1.03 (0.82-1.31) | | 2.84 (1.96-4.12) | | 7.55 (5.05-11.3) |
| | Control | 1.23 (0.94-1.64) | 0.83 (0.58-1.20) | 3.05 (2.01-4.62) | 0.93 (0.54-1.62) | 5.00 (3.19-7.85) |
| PS 6B - OPA | CPG 7909 | 8 (6-9) | | 66 (45-96) | | 268 (187-384) |
| | Control | 8 (6-10) | 0.93 (0.67-1.28) | 82 (54-124) | 0.81 (0.46-1.40) | 184 (136-248) |
| PS 9V - IgG | CPG 7909 | 0.50 (0.42-0.60) | | 2.48 (1.71-3.58) | | 3.69 (2.65-5.15) |
| | Control | 0.70 (0.51-0.97) | 0.71 (0.50-1.03) | 2.22 (1.52-3.25) | 1.11 (0.66-1.88) | 2.71 (1.91-3.86) |
| PS 14 - IgG | CPG 7909 | 1.92 (1.43-2.57) | | 9.54 (6.40-14.2) | | 10.03 (6.84-14.7) |
| | Control | 2.38 (1.67-3.39) | 0.80 (0.51-1.27) | 9.99 (6.31-15.8) | 0.96 (0.52-1.74) | 11.2 (7.43-16.8) |
| PS 14 - OPA | CPG 7909 | 37 (25-54) | | 343 (261-454) | | 351 (274-449) |
| | Control | 32 (22-46) | 1.17 (0.69-1.98) | 342 (253-462) | 1.01 (0.67-1.51) | 318 (249-405) |
| PS 18C - IgG | CPG 7909 | 0.75 (0.61-0.93) | | 4.11 (2.89-5.85) | | 4.61 (3.33-6.37) |
| | Control | 1.00 (0.76-1.30) | 0.76 (0.54-1.06) | 4.59 (3.20-6.60) | 0.90 (0.54-1.47) | 4.88 (3.50-6.80) |
| PS 19F - IgG | CPG 7909 | 1.38 (1.12-1.71) | | 3.10 (2.36-4.07) | | 4.79 (3.64-6.30) |
| | Control | 2.09 (1.62-2.70) | 0.66 (0.48-0.92) | 4.52 (3.37-6.05) | 0.69 (0.46-1.02) | 5.24 (3.95-6.96) |
| PS 19fF OPA | CPG 7909 | 25 (15-39) | | 428 (306-601) | | 329 (255-426) |
| | Control | 20 (13-32) | 1.21 (0.64-2.28) | 359 (250-510) | 1.20 (0.74-1.95) | 242 (186-314) |
| PS 23F - IgG | CPG 7909 | 0.69 (0.57-0.83) | | 2.76 (1.94-3.94) | | 6.81 (4.89-9.48) |
| | Control | 0.75(0.61-0.92) | 0.92(0.70-1.21) | 3.82 (2.52-5.79) | 0.72 (0.42-1.24) | 5.88 (3.85-9.00) |
| PS 23F - OPA | CPG 7909 | 13(10-17) | | 1.07(72-160) | | 196(147-260) |
| | Control | 11(8-13) | 1.22(0.86-1.74) | 132(89-194) | 0.81(0.47-1.41) | 1.73(129-232) |

| PCV-7 serotypes | Group | GM-ratio | Pre PPV-23 | GM-ratio | Post PPV-23 | GM-ratio |
|---|---|---|---|---|---|---|
| PS 4 - IgG | CPG 7909 | | 1.00 (0.72-1.39) | | 1.86 (1.34-2.57) | |
| | Control | 1.53 (1.00-2.37) | 0.71 (0.53-0.96) | 1.40 (0.91-2.16) | 1.45 (1.07-1.96) | 1.28 (0.83-1.98) |
| PS 6B - IgG | CPG 7909 | | 3.55 (2.47-5.12) | | 5.21 (3.64-7.46) | |
| | Control | 1.51 (0.83-2.75) | 2.62 (1.71-4.01) | 1.36 (0.77-2.38) | 4.07 (2.66-6.24) | 1.28 (0.73-2.24) |
| PS 6B - OPA | CPG 7909 | | 268 (195-370) | | 556 (399-774) | |
| | Control | 1.46 (0.92-2.31) | 276 (200-379) | 0.97 (0.62-1.52) | 505 (377-674) | 1.10 (0.72-1.70) |
| PS 9V - IgG | CPG 7909 | | 1.83 (1.30-2.58) | | 3.50 (2.59-4.72) | |
| | Control | 1.36 (0.84-2.20) | 1.41 (0.97-2.07) | 1.30 (0.78-2.15) | 2.63 (1.85-3.74) | 1.33 (0.84-2.12) |
| PS 14 - IgG | CPG 7909 | | 7.31 (4.33-9.18) | | 9.76 (7.16-13.3) | |
| | Control | 0.90 (0.51-1.56) | 7.64 (5.13-11.4) | 0.83 (0.48-1.42) | 10.1 (6.96-14.7) | 0.98 (0.59-1.57) |
| PS 14 - OPA | CPG 7909 | | 617 (475-802) | | 538 (385-752) | |
| | Control | 1.10 (0.78-1.55) | 576 (445-746) | 1.07 (0.74-1.54) | 339 (243-471) | 1.62 (1.01-2.59) |
| PS 18C - IgG | CPG 7909 | | 2.46 (1.75-3.47) | | 3.96 (3.05-5.14) | |
| | Control | 0.94 (0.60-1.49) | 2.82 (2.03-3.94) | 0.87 (0.54-1.40) | 3.91 (2.88-5.30) | 1.01 (0.68-1.51) |
| PS 19F - IgG | CPG 7909 | | 2.89 (2.19-3.81) | | 5.57 (4.40-7.05) | |
| | Control | 0.91 (0.62-1.35) | 3.10 (2.33-4.11) | 0.93 (0.63-1.38) | 6.30 (4.59-8.63) | 0.88 (0.59-1.32) |
| PS 19fF OPA | CPG 7909 | | 204 (142-293) | | 701 (530-926) | |
| | Control | 1.36 (0.95-1.96) | 205 (147-286) | 1.00 (0.61-1.61) | 551 (385-789) | 1.26 (0.79-2.00) |

TABLE 4-continued

Geometric mean concentrations of IgG antibodies and geometric mean of OPA titers
of persons with HIV receiving pneumococcal vaccines with or without CPG 7909.

| PS 23F - IgG | CPG 7909 | | 3.36 (2.43-4.65) | | 5.14 (3.91-6.76) | |
|---|---|---|---|---|---|---|
| | Control | 1.16(0.68-1.98) | 2.98(2.01-4.40) | 1.13(0.68-1.86) | 4.09(2.85-5.89) | 1.25(0.79-1.99) |
| PS 23F - OPA | CPG 7909 | | 2.44(184-323) | | 3.62(246-533) | |
| | Control | 1.13(0.75-1.69) | 205(154-273) | 1.19(0.87-1.77) | 245(171-351) | 1.47(0.87-2.48) |

| Non-PCV-7 serotypes[a] | Group | Pre-PCV1 | GM-ratio | Post-PCV1 | GM-ratio | Post-PCV2 |
|---|---|---|---|---|---|---|
| PS 1 - IgG | CPG 7909 | 0.43 (0.34-0.54) | | 0.38 (0.30-0.47) | | 0.37 (0.30-0.47) |
| | Control | 0.48 (0.39-0.59) | 0.88 (0.65-1.19) | 0.47 (0.39-0.57) | 0.80 (0.60-1.06) | 0.43 (0.37-0.50) |
| PS 7F - IgG | CPG 7909 | 0.78 (0.58-1.05) | | 0.56 (0.42-0.74) | | 0.46 (0.34-0.62) |
| | Control | 0.92 (0.72-1.19) | 0.85 (0.58-1.24) | 0.70 (0.54-0.90) | 0.80 (0.54-1.16) | 0.66 (0.53-0.84) |
| PS 19A - IgG | CPG 7909 | 1.55 (1.19-2.02) | | 2.10 (1.54-2.87) | | 2.58 (1.85-3.60) |
| | Control | 1.73 (1.27-2.35) | 0.90 (0.60-1.34) | 2.34 (1.69-3.24) | 0.90 (0.58-1.40) | 2.81 (1.95-4.05) |

| Non-PCV-7 serotypes[a] | Group | GM-ratio | Pre-PPV23 | GM-ratio | Post-PPV23 | GM-ratio |
|---|---|---|---|---|---|---|
| PS 1 - IgG | CPG 7909 | | 0.37 (0.28-0.49) | | 1.68 (1.18-2.39) | |
| | Control | 0.87 (0.66-1.15) | 0.51 (0.40-0.65) | 0.73 (0.51-1.03) | 2.29 (1.61-3.27) | 0.73 (0.45-1.20) |
| PS 7F - IgG | CPG 7909 | | 0.57 (0.40-0.82) | | 2.72 (1.74-4.25) | |
| | Control | 0.70 (0.48-1.00) | 0.60 (0.46-0.77) | 0.96 (0.63-1.47) | 2.94 (2.08-4.16) | 0.92 (0.53-1.60) |
| PS 19A - IgG | CPG 7909 | | 1.82 (1.31-2.53) | | 4.09 (2.76-6.07) | |
| | Control | 0.92 (0.56-1.50) | 1.86 (1.29-2.70) | 0.98 (0.60-1.60) | 4.69 (3.00-7.33) | 0.87 (0.48-1.58) |

Participants were immunized with double doses of PCV-7 (Prevnar ®, Wyeth) ±1 mg CPG 7909 at 0 and 3 months followed by single dose PPV-23 (Pneumo Novum ®, Sanofi-Pasteur MSD) ±1 mg CPG 7909 at 9 months.
[a]All included in PPV-23. OPA: opsonophacytic activity; PS: pneumococcal serotype; GM-ratio: geometric mean ratio; PCV-7: 7-valent pneumococcal conjugate vaccine; PPV-23: 23-valent pneumococcal polysaccharide vaccine;

As shown in table 2, mild systemic and injection site reactions to PCV were more common in the CpG group (100% vs 81.3%, p=0.002). Moderate to severe influenza-like symptoms were observed in the CpG group after PPV.

Figure 6:
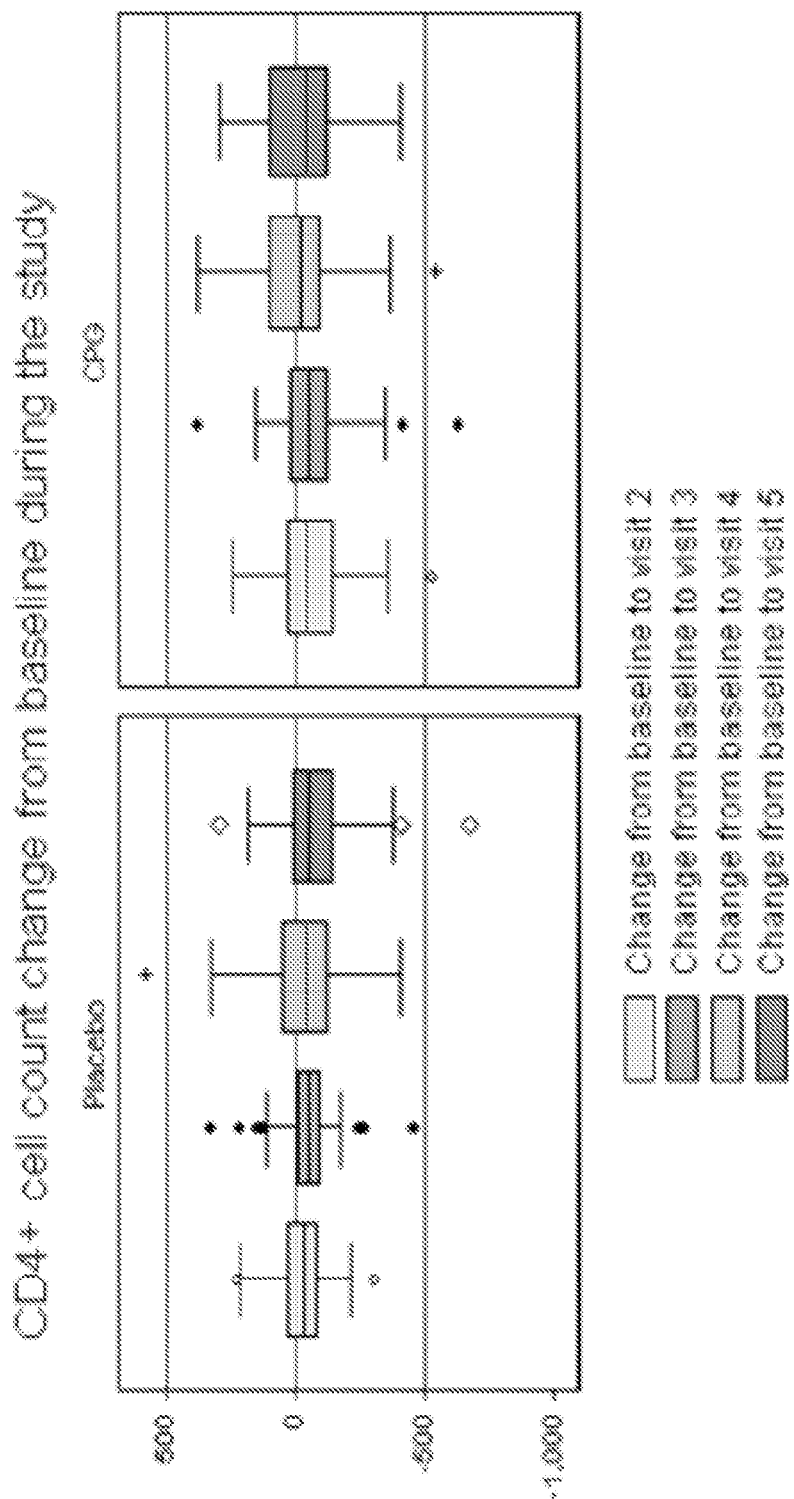
FIG. 6 shows the CD4+ cell count change as compared to baseline that occurred in both the CPG-7909 and placebo groups.

No adverse effects on CD4+ cell count (see FIG. 6) or organ functions occurred in either group.

TABLE 2

Injection-related adverse events.

| | First PCV | | | Second PCV | | | PPV-25 | | |
|---|---|---|---|---|---|---|---|---|---|
| | PCV | PCV + CPG | p | PCV | PCV + CPG | p | PPV-23 | PPV-23 + CPG | p |
| n (%) | n = 48 | n = 47 | | n = 48 | n = 44 | | n = 47 | n = 41 | |
| At least one adverse event | 33 (66.8) | 44 (93.6) | 0.002 | 30 (62.5) | 40 (90.9) | 0.001 | 28 (59.6) | 41 (100) | <0.001 |
| Injection site pain | 32 (66.7) | 45 (91.5) | 0.003 | 30 (62.5) | 57 (84.1) | 0.02 | 27 (57.5) | 36 (87.8) | 0.002 |
| Injection site erythema | 3 (8.3) | 10 (21.3) | 0.04 | 5 (10.4) | 11 (25.0) | 0.07 | 7 (14.9) | 25 (51.0) | <0.001 |
| Injection site bruising | 6 (12.5) | 18 (36.8) | 0.004 | 7 (14.5) | 15 (36.4) | 0.02 | 9 (19.2) | 27 (65.9) | <0.001 |
| Injection site itch | 0 (0) | 1 (2.1) | 0.50 | 0 (0) | 1 (2.3) | 0.48 | 0 (0) | 3 (7.3) | 0.10 |
| Influenza-like symptoms* | 3 (5.3) | 17 (36.2) | <0.001 | 3 (5.3) | 17 (38.5) | <0.001 | 2 (4.3) | 37 (90.2) | <0.001 |
| Headache | 2 (4.2) | 1 (2.1) | 1.00 | 0 (0) | 0 (0) | 1.00 | 0 (0) | 9 (5.7) | 0.02 |
| Nausea | 2 (4.2) | 1 (2.1) | 1.00 | 0 (0) | 1 (2.3) | 0.48 | 1 (2.1) | 0 (0) | 1.00 |

*Influenza-like symptoms included pyrexia, arthralgia, chills and fatigue

Conclusions: In a population known to be hypo-responsive to immunization the addition of CPG 7909 to a conjugate pneumococcal vaccine greatly enhanced the proportion of vaccine high-responders.

The safety of CPG 7909 and conjugate pneumococcal vaccine (Prevnar) was good and no adverse effects on organ functions or HIV disease progression were observed during the trial. The combination of CPG 7909 and conjugate pneumococcal vaccine (Prevnar) was well tolerated and adverse events were mild injection-site reactions and influenza-like symptoms. In this trial, CPG 7909 did not appear to increase the response to non-Prevnar serotypes following pneumococcal polysaccharide vaccination.

Example 3

TLR9-Agonist Adjuvant Induces Cellular Memory in Response to Pneumococcal Conjugate Vaccine in HIV-Infected Adults We examined how CPG 7909, affected the induction of cellular memory in response to pneumococcal conjugate vaccine.

Methods: Periferal blood mononuclear cells (PBMC) from 40 HIV-infected individuals from the double-blind, placebo-controlled phase Ib/IIa trial of Example 1 (20 subjects in each group) were collected at month 0 and 4 and were stored (frozen).

The Frozen PBMCs were thawed and tested for viability and transferred to 96-well flat-bottomed tissue culture plates.

The cells were incubated overnight at 37° C., and stimulated the following day with purified pneumococcal polysaccharide (serotype (ST) 6B and 14). After 48 hours incubation, the supernatants were harvested and cytokine concentrations measured by Luminex. The relative response was calculated as the ratio between cytokine concentrations post- and pre-immunization, taking pre-existing immunity to *Streptococcus pneumoniae* into account, as well as eliminating bias from innate recognition.

Figure 7:
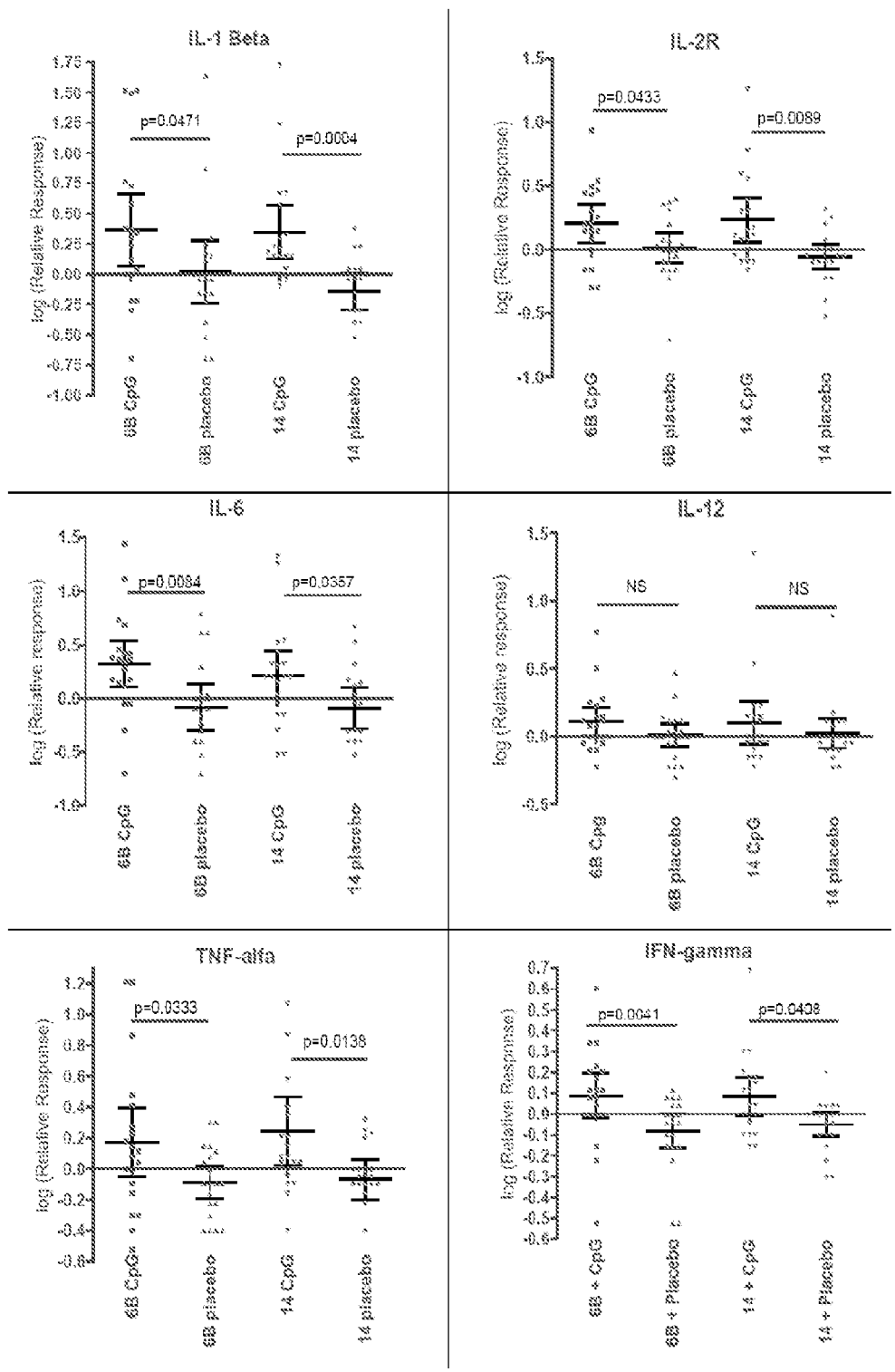
FIG. 7 shows relative response for cytokines IL-1 Beta, IL-2R, IL-6, IL-12, TNF-alfa, and IFN-gamma between the CPG-7909 and placebo groups for serotypes 6B and 14 as described in Example 3.
Figure 8:
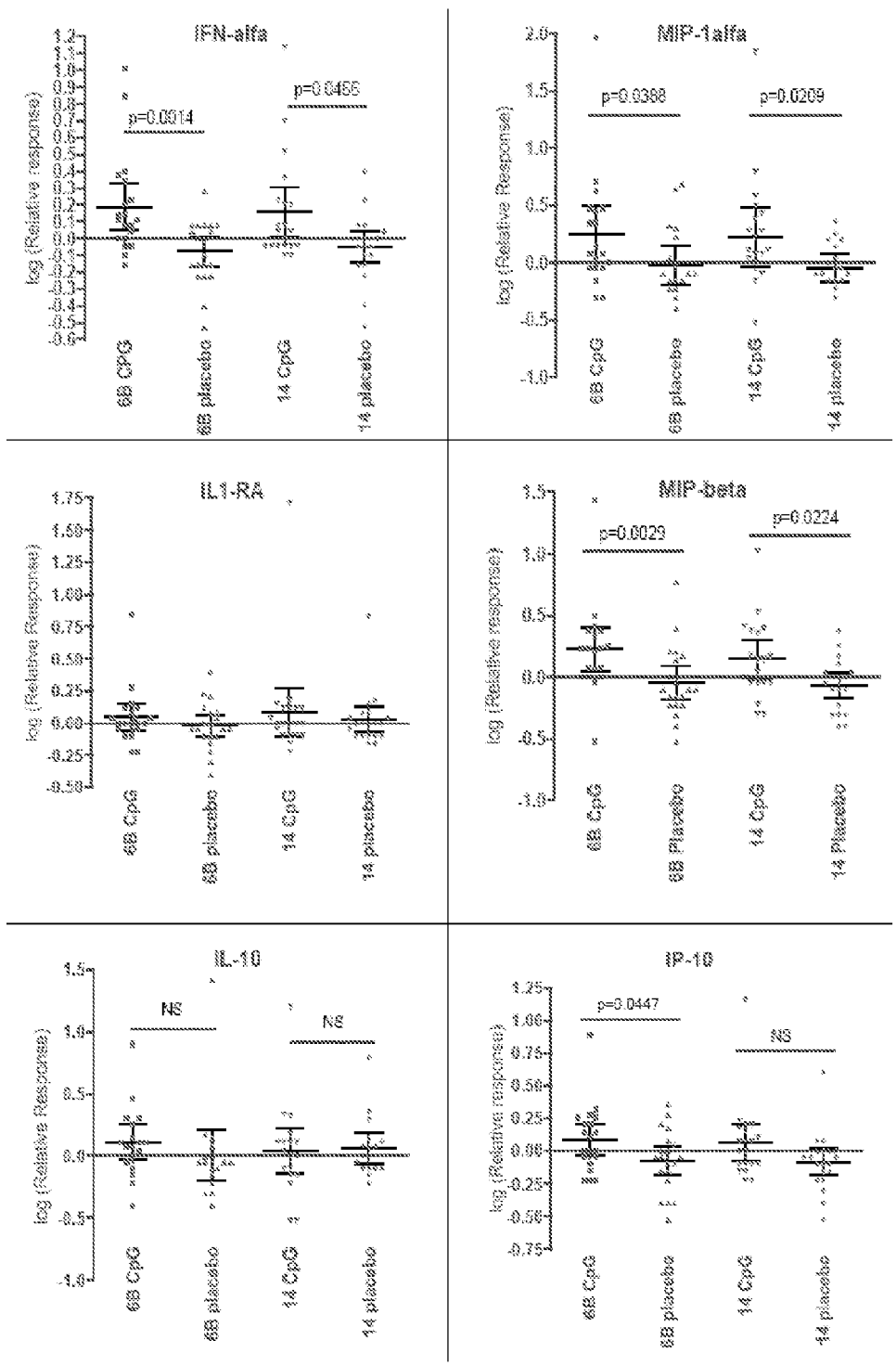
FIG. 8 shows relative response for cytokines IFN-alfa, MIP-1 alfa, IL1-RA, MIP-beta, IL-10, and IP-10 between the CPG-7909 and placebo groups for serotypes 6B and 14 as described in Example 3.
Figure 9:
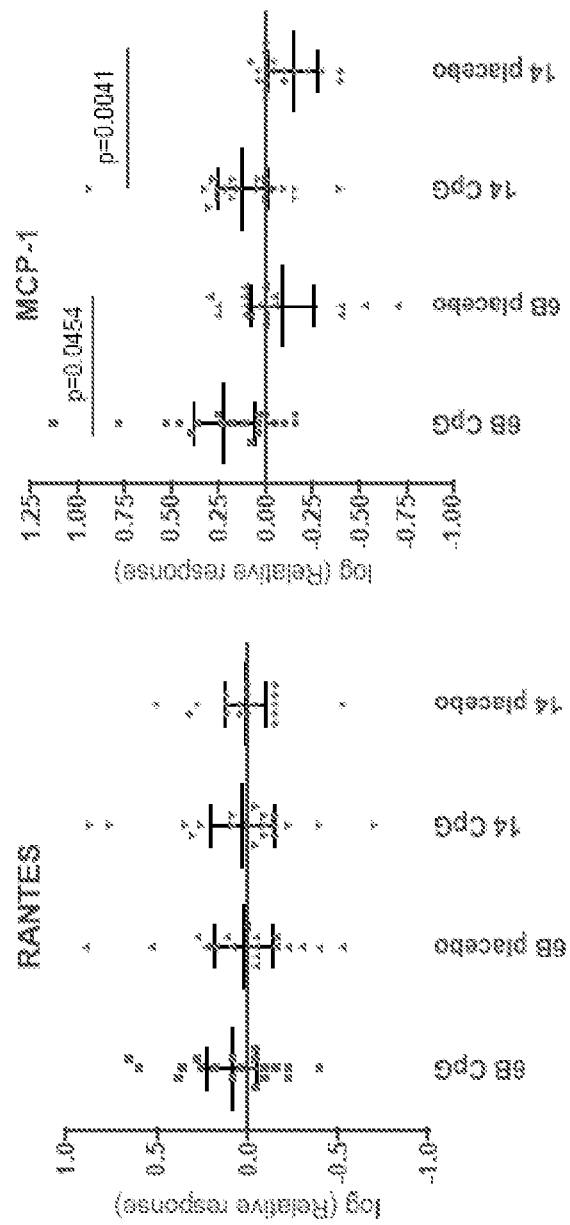
FIG. 9 shows relative response for cytokines RANTES and MCP-1 between the CPG-7909 and placebo groups for serotypes 6B and 14 as described in Example 3.

Results: As shown in FIGS. 7, 8 and 9, one month after the second pneumococcal conjugate vaccine the CPG 7909 group had a significantly higher relative cytokine response than the placebo-adjuvant group for IFN-gamma (ST6B): 1.22 vs. 0.82, p=0.004; (ST14): 1.21 vs. 0.89, p=0.04; TNF-alfa (ST6B): 1.49 vs. 0.82, p=0.03; (ST14): 1.76 vs. 0.85, p=0.01); IL-6 (ST6B): 2.11 vs. 0.83, p=0.0084; (ST14): 1.64 vs. 0.81, p=0.0357), IFN-alfa (ST6B): 1.55 vs. 0.84, p=0.0014; (ST14): 1.43 vs. 0.90, p=0.0466). Cytokine responses in the CPG 7909 group compared to the control group were also significantly increased observed for IL-1B, IL-2R, MIP-1alfa, MIP-beta, MCP-1 and IP-10.

Conclusion: Our results show that among people with HIV, a TLR9 agonist-adjuvant co-administered with pneumococcal conjugate vaccine induced cellular memory to pneumococcal polysaccharides which was not observed when the vaccine was administered alone.

The invention claimed is:

1. A method of immunizing a subject against diseases caused by *S. pneumoniae* infection comprising administering to said subject:
an immunoprotective dose of a vaccine comprising conjugated capsular *S. pneumoniae* saccharide antigens from serotypes 4, 6B, 9V, 14, 18C, 19F, and 23F; and
at least one TLR-9 agonist as an adjuvant, wherein said at least one TLR-9 agonist is a CpG oligonucleotide having the nucleic acid sequence selected from the group consisting of: 5' TCGTCGTTTTCGGTGCTTTT 3' (SEQ ID NO: 3); 5' TCGTCGTTTTTCGGTCGTTTT 3' (SEQ ID NO: 4); 5' TCGTCGTTTTGTCGTTTTGTCGTT 3' (SEQ ID NO: 5); 5' TCGTCGTTTCGTCGTTTTGTCGTT 3' (SEQ ID NO: 6); and 5' TCGTCGTTTTGTCGTTTTTTCGA 3' (SEQ ID NO: 7);

and wherein said subject suffers from HIV-infection or acquired immunodeficiency syndrome (AIDS).

2. The method of claim 1, wherein said subject is a mammal.

3. The method of claim 2, wherein said mammal is a cat, sheep, pig, horse, bovine, dog, rat, mouse or a human.

4. The method according to claim 1, wherein the subject is a human adult at least 55 years of age.

5. The method of claim 1, wherein an internucleotide linkage of the CpG oligonucleotide is phosphodiester, phosphorothioate, methylphosphonate, methylphosphorothioate, phosphorodithioate, p-ethoxy, or combinations thereof.

6. The method of claim 1, wherein the vaccine comprises S. pneumoniae saccharides from serotypes 1, 3, 4, 5, 6A, 6B, 7F, 9V, 14, 18C, 19A, 19F and 23F.

7. The method of claim 1, wherein the capsular saccharide antigens are conjugated to a carrier protein selected from the group consisting of: TT, DT, CRM197, fragment C of TT, PhtD, PhtDE fusions, detoxified pneumolysin, and protein D.

8. The method of claim 1, wherein the capsular saccharide antigens are all individually conjugated to the same carrier protein.

9. The method of claim 8, wherein the carrier protein is CRM197.

10. The method according to claim 1, wherein said CpG oligonucleotide is selected from the group consisting of:

5' T*C*G*T*C*G*T*T*T*T*T*C*G*G*T*G*C*T*T*T*T 3' (SEQ ID NO 8),

5' T*C*G*T*C*G*T*T*T*T*T*C*G*G*T*C*G*T*T*T*T 3' (SEQ ID NO 9),

5' T*C*G*T*C*G*T*T*T*T*G*T*C*G*T*T*T*T*G*T*C*G*T*T 3' (SEQ ID NO 10),

5' T*C*G*T*C*G*T*T*T*C*G*T*C*G*T*T*T*T*G*T*C*G*T*T 3' (SEQ ID NO 11), and

5' T*C*G*T*C*G*T*T*T*T*G*T*C*G*T*T*T*T*T*T*C*G*A 3' (SEQ ID NO: 12), wherein * refers to a phosphorothioate bond.

11. The method according to claim 1, wherein the at least one TLR-9 agonist is present in an amount ranging from 0.2 mg to 10 mg.

12. The method according to claim 1, wherein each conjugate saccharide antigen of the vaccine is present in an amount ranging from 2 to 100 μg.

13. The method according to claim 12, wherein each saccharide antigen of the vaccine is present in an amount ranging from 1 to 5 μg.

14. The method according to claim 1, wherein said vaccine comprises sodium chloride and/or sodium succinate buffer as excipient(s).

15. The method according to claim 1, wherein alum, aluminium hydroxide, aluminium phosphate, or aluminium sulphate is further administered in addition to the at least one TLR-9 agonist as adjuvant.

* * * * *